United States Patent
Neumann et al.

(10) Patent No.: US 6,525,041 B1
(45) Date of Patent: *Feb. 25, 2003

(54) MANGANESE OR IRON COMPLEXES OF NITROGEN-CONTAINING MACROCYCLIC LIGANDS EFFECTIVE AS CATALYSTS FOR DISMUTATING SUPEROXIDE

(75) Inventors: William L. Neumann, Kirkwood, MO (US); Dennis P. Riley, Ballwin, MO (US); Randy H. Weiss, St. Louis, MO (US); Susan L. Henke, Webster Groves, MO (US); Patrick J. Lennon, Clayton, MO (US); Karl W. Aston, Pacific, MO (US)

(73) Assignee: Pharmacia Corporation, St. Louis, MO (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

This patent is subject to a terminal disclaimer.

(21) Appl. No.: 08/596,887

(22) Filed: Mar. 14, 1996

Related U.S. Application Data

(63) Continuation-in-part of application No. 08/468,854, filed on Jun. 6, 1995, now abandoned.

(51) Int. Cl.$^7$ ..................... A61K 31/555; C07D 259/00
(52) U.S. Cl. ................. 514/184; 514/185; 540/465
(58) Field of Search ............................ 514/184, 185; 540/465

(56) References Cited

U.S. PATENT DOCUMENTS

| | | | |
|---|---|---|---|
| 3,930,867 A | 1/1976 | Bigelow ............... | 540/460 |
| 4,001,212 A | 1/1977 | Richman ............... | 540/460 |
| 4,702,998 A | 10/1987 | Tanaka et al. ............... | 540/460 |
| 4,885,363 A | 12/1989 | Tweedle et al. ............... | 540/465 |
| 5,096,724 A | 3/1992 | Zenner et al. ............... | 426/124 |
| 5,637,578 A | * 6/1997 | Riley et al. ............... | 514/186 |
| 5,721,361 A | * 2/1998 | Lennon et al. ............... | 540/450 |
| 5,874,421 A | * 2/1999 | Riley et al. ............... | 514/161 |

FOREIGN PATENT DOCUMENTS

| | | |
|---|---|---|
| AU | 14611 | 10/1988 |
| EP | 284645 | 10/1988 |
| EP | 374929 | 6/1990 |
| EP | 391766 | 10/1990 |
| EP | 436189 | 7/1991 |
| EP | 0 524 161 A1 | 1/1993 |
| JP | 59-193 824 A | 4/1983 |
| JP | 5 9098074 | 6/1984 |
| WO | WO 89/12119 | 12/1989 |
| WO | WO 91/10645 | 7/1991 |
| WO | WO 93/06868 | 4/1993 |
| WO | 9415925 | 7/1994 ............... 540/465 |
| WO | WO 95/28968 | * 11/1995 |

OTHER PUBLICATIONS

Material and Safety Data Sheet for hydrazine, EM Science Oct. 30, 1996.*
Material and Safety Data Sheet for triethylphosphin, OSHA Apr. 15, 1999.*
Seccombe et al., PubMed Abstract (J. Thorac. Cardiovasc. Surg. 107(2):505–9, Feb. 1994).*
Hans, PubMed Abstract (Ann. Fr. Anesth. Reanim. 15(3):374–81, 1996).*
Melon, PubMed Abstract (J. Neuroradiol. 26(1 suppl):S30–5, Mar. 1999).*
Newton, J.E. et al., Synthesis and Characterization of the Mn(II) Complex of [15]ane $N_5$, *J. Coord. Chem.*, vol. 19, pp. 265–277 (1988).
Weiss, R.H. et al, Catalytic Efficacies of Agents that Dismutate Superoxide, *J. Cell. Biochem.*, Suppl. 15C, 216, abstract CC110 (1991).
Petkau, A., Scientific Basis for the Clinical Use of Superoxide Dismutase, *Cancer Treat. Rev.*, vol. 13, pp. 17–44 (1986).
McCord, J.M., Superoxide Dismutase: Rationale for Use in Reperfusion Injury and Inflammation, *J. Free Radicals Biol. Med.*, vol. 2, pp. 307–310 (1986).
Bannister, J.V. et al., Aspects of the Structure, Function, and Applications of Superoxide Dismutase, *CRC Crit. Reviews in Biochem.*, vol. 22, Issue 2, pp. 111–180 (1987).
Richman, J.E. et al., Nitrogen Analogs of Crown Ethers, *J. Am. Chem. Soc.*, vol. 96, pp. 2268–2270 (1974).

(List continued on next page.)

*Primary Examiner*—Deepak Rao
(74) *Attorney, Agent, or Firm*—Sonnenschein Nath & Rosenthal

(57) ABSTRACT

Low molecular weight mimics of superoxide dismutase (SOD) represented by the formula:

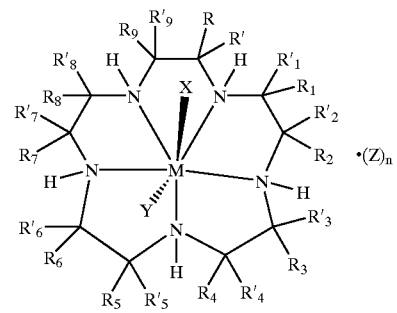

wherein R, R', $R_1$, $R'_1$, $R_2$, $R'_2$, $R_3$, $R'_3$, $R_4$, $R'_4$, $R_5$, $R'_5$, $R_6$, $R'_6$, $R_7$, $R'_7$, $R_8$, $R'_8$, $R_9$, and $R'_9$, M, X, Y, Z and n are as defined herein, useful as therapeutic agents for inflammatory disease states and disorders, ischemic/reperfusion injury, stroke, atherosclerosis, and all other conditions of oxidant-induced tissue damage or injury.

21 Claims, No Drawings

OTHER PUBLICATIONS

Atkins, T.J. et al., Macrocyclic Polyamines: 1,4,7,10,13, 16–Hexaazacyclooctadecane, *Org. Synth.*, vol. 58, pp. 86–98 (1978).

Riley, D.P. et al., Stopped–Flow Kinetic Analysis for Monitoring Superoxide Decay in Aqueous System, *Anal. Biochem.*, vol. 196, pp. 334–349 (1991).

Bull, C. et al., The Mechanism of Fe–EDTA Catalyzed Superoxide Dismutation, *J. Am. Chem. Soc.*, vol. 105, pp. 5290–5300 (1983).

Kimura, E. et al., Further Studies on Superoxide Dismutase Activities of Macrocyclic Polyamine Complexes of Copper (II), *Biochem. Biophys. Acta*, vol. 745, pp. 37–43 (1983).

Kimura, E. et al., Superoxide Dismutase Activity of Macrocyclic Polyamine Complexes, *Biochim. Biophys. Acta*, vol. 678, pp. 172–179 (1981).

Rush, J.D. et al., The Superoxide Dismutase Activities of Two Higher–Valent Manganese Complexes, $Mn^{IV}$ Desferrioxamine and $MN^{III}$ Cyclam[1], *Arch. Biochem. Biophys.*, vol. 289, No. 1, pp. 1–6 (1991).

Fretland, D.J. et al., Superoxide Dismutase (SOD) Modulates Acetic Acid–Induced Colitis in Rodents, *Gastronenterology*, vol. 100, p. A581 (1990).

Gryglewski, R.J. et al., Superoxide Anion is Involved in the Breakdown of Endothelium–Derived Vascular Relaxing Factor, *Nature*, vol. 320, pp. 454–456 (1986).

Alexander, M.D. et al, Manganese (II) Complexes of a Macrocyclic Ligand, *Inorg. Nucl. Chem. Letters*, vol. 6, pp. 445–448 (1970).

Brady, S.F. et al., Practical Synthesis of Cyclic Peptides, with an Example of Dependence of Cyclization Yield upon Linear Sequence, *J. Org. Chem.*, vol. 44, pp. 3101–3105 (1979), No. 18.

Tabushi, I. et al., Preparation of C–Alkylated Macrocyclic Polyamines, *Tetrahedron Letters*, No. 12, pp. 1049–1052 (1977).

Fujioka, H. et al., The Effects of Size and Donor Atoms of Macrocyclic Polyamines Binding to $Mg^{2+}$ and $Ca^{2+}$, *Chem. Letters*, pp. 737–740 (1982).

Krakowiak, K.E. et al., Preparation of Triaza–, Tetraaza–and Peraza–Crown Compounds Containing Aminoalkyl Side Groups or Unsubstituted Ring Nitrogen Atoms, *J. Org. Chem.*, vol. 55, pp. 3364–3368 (1990).

Bradshaw, J.S. et al., A Simple Crab–Like Cyclization Procedure to Prepare Polyaza–Crowns and Cyclams with one or two unsubstituted Macroring Nitrogen Atoms or With a Hydroxy Group, *J. Heterocyclic Chem.*, vol. 26, pp. 1431–1435 (1989).

Krakowiak, K.E. et al., Novel Syntheses of Monofunctionalized Triaza–Crowns and Cyclams with a Secondary Amine Group on a Side Chain, *Tetrahedron Letters*, vol. 30, No. 22, pp. 2897–2900 (1989).

Krakowiak, K.E. et al., Preparation and Structural Properties of Large–Cavity Peraza Macrocycles Containing Pyridine, Phenanthroline, or Piperazine Subcyclic Units, *J. Org. Chem.*, vol. 56, pp. 2675–2680 (1991).

Jackels, S.C., et al., Aqueous Proton NMR Relazation Enhancement by Manganese (II) Macrocyclic Complexes: Structure–Relaxivity Relationships, *Inorg. Chem.* vol. 31, No. 2, pp. 234–239, (1992).

Lindoy, Leonard F., The Chemistry of Macrocyclic Ligand Complexes, Cambridge University Press, pp. 16–17 and 40–43 (1989).

* cited by examiner

MANGANESE OR IRON COMPLEXES OF NITROGEN-CONTAINING MACROCYCLIC LIGANDS EFFECTIVE AS CATALYSTS FOR DISMUTATING SUPEROXIDE

This application is a continuation-in-part of application Ser. No. 08/468,854, filed Jun. 6, 1995 now abandoned.

BACKGROUND OF THE INVENTION

1. Field of the Invention

The present invention relates to compounds effective as catalysts for dismutating superoxide and, more particularly, relates to manganese or iron complexes of nitrogen-containing fifteen-membered macrocyclic ligands which catalytically dismutate superoxide.

2. Related Art

The enzyme superoxide dismutase catalyzes the conversion of superoxide into oxygen and hydrogen peroxide according to equation (1) (hereinafter referred to as dismutation). Reactive oxygen metabolites derived from superoxide are postulated to contribute to the tissue pathology in a number of

$$O_2^- + O_2^- + 2H^+ \rightarrow O_2 + H_2O_2 \quad (1)$$

inflammatory diseases and disorders, such as reperfusion injury to the ischemic myocardium, inflammatory bowel disease, rheumatoid arthritis, osteoarthritis, atherosclerosis, hypertension, metastasis, psoriasis, organ transplant rejections, radiation-induced injury, asthma, influenza, stroke, burns and trauma. See, for example, Bulkley, G. B., Reactive oxygen metabolites and reperfusion injury: aberrant triggering of reticuloendothelial function, *The Lancet*, Vol. 344, pp. 934–36, Oct. 1, 1994; Grisham, M. B., Oxidants and free radicals in inflammatory bowel disease, *The Lancet*, Vol. 344, pp. 859–861, Sep. 24, 1994; Cross, C. E. et al., Reactive oxygen species and the lung, *The Lancet*, Vol. 344, pp. 930–33, Oct. 1, 1994; Jenner, P., Oxidative damage in neurodegenerative disease, *The Lancet*, Vol. 344, pp. 796–798, Sep. 17, 1994; Cerutti, P. A., Oxy-radicals and cancer, *The Lancet*, Vol. 344, pp. 862–863, Sep. 24, 1994 Simic, M. G., et al, Oxygen Radicals in Biology and Medicine, Basic Life Sciences, Vol. 49, Plenum Press, New York and London, 1988; Weiss J. Cell. Biochem., 1991 Suppl. 15C, 216 Abstract C110 (1991); Petkau, A., Cancer Treat. Rev. 13, 17 (1986); McCord, J. Free Radicals Biol. Med., 2, 307 (1986); and Bannister, J. V. et al, Crit. Rev. Biochem., 22, 111 (1987). The above-identified references from *The Lancet* teach the nexus between free radicals derived from superoxide and a variety of diseases. In particular, the Bulkley and Grisham references specifically teach that there is a nexus between the dismutation of superoxide and the final disease treatment.

It is also known that superoxide is involved in the breakdown of endothelium-derived vascular relaxing factor (EDRF), which has been identified as nitric oxide (NO), and that EDRF is protected from breakdown by superoxide dismutase. This suggests a central role for activated oxygen species derived from superoxide in the pathogenesis of vasospasm, thrombosis and atherosclerosis. See, for example, Gryglewski, R. J. et al., "Superoxide Anion is Involved in the Breakdown of Endothelium-derived Vascular Relaxing Factor", *Nature*, Vol. 320, pp. 454–56 (1986) and Palmer, R. M. J. et al., "Nitric Oxide Release Accounts for the Biological Activity of Endothelium Derived Relaxing Factor", *Nature*, Vol. 327, pp. 523–26 (1987).

Clinical trials and animal studies with natural, recombinant and modified superoxide dismutase enzymes have been completed or are ongoing to demonstrate the therapeutic efficacy of reducing superoxide levels in the disease states noted above. However, numerous problems have arisen with the use of the enzymes as potential therapeutic agents, including lack of oral activity, short half-lives in vivo, immunogenicity with nonhuman derived enzymes, and poor tissue distribution.

SUMMARY OF THE INVENTION

It is an object of the invention to provide manganese or iron complexes of nitrogen-containing fifteen-membered macrocyclic ligands that are low molecular weight mimics of superoxide dismutase (SOD) which are useful as therapeutic agents for inflammatory disease states or disorders which are mediated, at least in part, by superoxide. It is a further object of the invention to provide manganese (II) or iron (III) complexes of nitrogen-containing fifteen-membered macrocyclic ligands which are useful as magnetic resonance imaging (MRI) contrast agents having improved kinetic stability, improved oxidative stability and improved hydrogen bonding. It is yet a further object of the invention to provide MRI contrast agents in which the biodistribution of the contrast agents can be controlled.

According to the invention, manganese or iron complexes of nitrogen-containing fifteen-membered macrocyclic ligands are provided in which at least one adjacent pair of carbon atoms in the macrocyclic ligand are substituted with alkyl, alkenyl, alkynyl, cycloalkyl or cycloalkenyl radicals wherein at least one of the substituents on the adjacent carbons is substituted with —$OR_{10}$, —$NR_{10}R_{11}$, —$COR_{10}$, —$CO_2R_{10}$, —$CONR_{10}R_{11}$, —O—(—$(CH_2)_a$—O)$_b$—$R_{10}$, —$SR_{10}$, —$SOR_{10}$, —$SO_2R_{10}$, —$SO_2NR_{10}R_{11}$, —$N(OR_{10})(R_{11})$, —$P(O)(OR_{10})(OR_{11})$, —$P(O)(OR_{10})(R_{11})$ and —OP(O)($OR_{10}$)($OR_{11}$) wherein $R_{10}$ and $R_{11}$ are independently selected from hydrogen or alkyl groups, and a and b are integers independently selected from 1 to 6.

DETAILED DESCRIPTION OF THE INVENTION

The present invention is directed to manganese or iron complexes of nitrogen-containing fifteen-membered macrocyclic ligands which catalyze the conversion of superoxide into oxygen and hydrogen peroxide. These complexes can be represented by the formula:

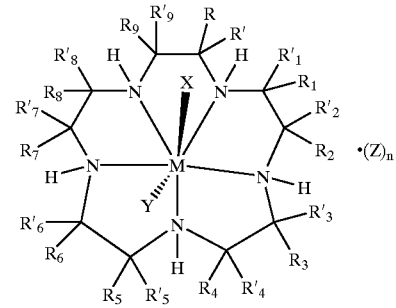

wherein at least one pair of "R" groups on adjacent carbon atoms of the macrocycle selected from the group consisting of $R_9$ or $R'_9$ and R or R', $R_1$ or $R'_1$ and $R_2$ or $R'_2$, $R_3$ or $R'_3$ and $R_4$ or $R'_4$, $R_5$ or $R'_5$ and $R_6$ or $R'_6$, and $R_7$ or $R'_7$ and $R_8$ or $R'_8$ are substituted alkyl, substituted alkenyl, substituted alkynyl, substituted cycloalkyl or substituted cycloalkenyl radicals wherein the substituents are independently selected from the group consisting of —$OR_{10}$, —$NR_{10}R_{11}$, —$COR_{10}$, —$CO_2R_{10}$, —$CONR_{10}R_{11}$, —O—(—$(CH_2)_a$—O)$_b$—$R_{10}$, —$SR_{10}$, —$SOR_{10}$, —$SO_2R_{10}$, —$SO_2NR_{10}R_{11}$, —$N(OR_{10})(R_{11})$, —$P(O)(OR_{10})(OR_{11})$, —$P(O)(OR_{10})(R_{11})$ and —$OP(O)(OR_{10})(OR_{11})$; or at least one pair of "R" groups on adjacent carbon atoms of the macrocycle selected from the group consisting of $R_9$ or $R'_9$ and R or R', $R_1$ or $R'_1$ and $R_2$ or $R'_2$, $R_3$ or $R'_3$ and $R_4$ or $R'_4$, $R_5$ or $R'_5$ and $R_6$ or $R'_6$, and $R_7$ or $R'_7$ and $R_8$ or $R'_8$ are independently selected wherein one "R" group of the pair is an alkyl, alkenyl, alkynyl, cycloalkyl or cycloalkenyl radical and the other "R" group on the adjacent carbon atom of the macrocycle is a substituted alkyl, substituted alkenyl, substituted alkynyl, substituted cycloalkyl or substituted cycloalkenyl radical wherein the substituents are independently selected from the group consisting of —$OR_{10}$, —$NR_{10}R_{11}$, —$COR_{10}$, —$CO_2R_{10}$, —$CONR_{10}R_{11}$, —O—(—$(CH_2)_a$—O)$_b$—$R_{10}$, —$SR_{10}$, —$SOR_{10}$, —$SO_2R_{10}$, —$SO_2NR_{10}R_{11}$, —$N(OR_{10})(R_{11})$, —$P(O)(OR_{10})(OR_{11})$, —$P(O)(OR_{10})(R_{11})$ and —$OP(O)(OR_{10})(OR_{11})$; or combinations thereof; wherein $R_{10}$ and $R_{11}$ are independently selected from the group consisting of hydrogen and alkyl groups, and a and b are integers independently selected from 1 to 6; and the remaining "R" groups are hydrogen or, optionally, are independently selected from the group consisting of alkyl, alkenyl, alkynyl, cycloalkyl, cycloalkenyl, cycloalkylalkyl, cycloalkylcycloalkyl, cycloalkenylalkyl, alkylcycloalkyl, alkenylcycloalkyl, alkylcycloalkenyl, alkenylcycloalkenyl, heterocyclic, aryl and aralkyl radicals and radicals attached to the α-carbon of α-amino acids; or $R_1$ or $R'_1$ and $R_2$ or $R'_2$, $R_3$ or $R'_3$ and $R_4$ or $R'_4$, $R_5$ or $R'_5$ and $R_6$ or $R'_6$, $R_7$ or $R'_7$ and $R_8$ or $R'_8$, and $R_9$ or $R'_9$ and R or R' together with the carbon atoms to which they are attached independently form a saturated, partially saturated or unsaturated cyclic having 3 to 20 carbon atoms; or R or R' and $R_1$ or $R'_1$, $R_2$ or $R'_2$ and $R_3$ or $R'_3$, $R_4$ or $R'_4$ and $R_5$ or $R'_5$, $R_6$ or $R'_6$ and $R_7$ or $R'_7$, and $R_8$ or $R'_8$ and $R_9$ or $R'_9$ together with the carbon atoms to which they are attached independently form a nitrogen containing heterocycle having 2 to 20 carbon atoms provided that when the nitrogen containing heterocycle is an aromatic heterocycle which does not contain a hydrogen attached to the nitrogen, the hydrogen attached to the nitrogen in said formula, which nitrogen is also in the macrocycle and the R groups attached to the same carbon atoms of the macrocycle are absent; and combinations thereof; wherein M is Mn or Fe.

The currently preferred optional "R" groups are alkyl radicals, radicals attached to the α-carbon of α-amino acids, and saturated, partially saturated or unsaturated cyclic ring structures having 3 to 20 carbon atoms. Currently, $R_{10}$ and $R_{11}$ are preferably hydrogen.

X, Y and Z represent suitable ligands or charge-neutralizing anions which are derived from any monodentate or polydentate coordinating ligand or ligand system or the corresponding anion thereof (for example benzoic acid or benzoate anion, phenol or phenoxide anion, alcohol or alkoxide anion). X, Y and Z are independently selected from the group consisting of halide, oxo, aquo, hydroxo, alcohol, phenol, dioxygen, peroxo, hydroperoxo, alkylperoxo, arylperoxo, ammonia, alkylamino, arylamino, heterocycloalkyl amino, heterocycloaryl amino, amine oxides, hydrazine, alkyl hydrazine, aryl hydrazine, nitric oxide, cyanide, cyanate, thiocyanate, isocyanate, isothiocyanate, alkyl nitrile, aryl nitrile, alkyl isonitrile, aryl isonitrile, nitrate, nitrite, azido, alkyl sulfonic acid, aryl sulfonic acid, alkyl sulfoxide, aryl sulfoxide, alkyl aryl sulfoxide, alkyl sulfenic acid, aryl sulfenic acid, alkyl sulfinic acid, aryl sulfinic acid, alkyl thiol carboxylic acid, aryl thiol carboxylic acid, alkyl thiol thiocarboxylic acid, aryl thiol thiocarboxylic acid, alkyl carboxylic acid (such as acetic acid, trifluoroacetic acid, oxalic acid), aryl carboxylic acid (such as benzoic acid, phthalic acid), urea, alkyl urea, aryl urea, alkyl aryl urea, thiourea, alkyl thiourea, aryl thiourea, alkyl aryl thiourea, sulfate, sulfite, bisulfate, bisulfite, thiosulfate, thiosulfite, hydrosulfite, alkyl phosphine, aryl phosphine, alkyl phosphine oxide, aryl phosphine oxide, alkyl aryl phosphine oxide, alkyl phosphine sulfide, aryl phosphine sulfide, alkyl aryl phosphine sulfide, alkyl phosphonic acid, aryl phosphonic acid, alkyl phosphinic acid, aryl phosphinic acid, alkyl phosphinous acid, aryl phosphinous acid, phosphate, thiophosphate, phosphite, pyrophosphite, triphosphate, hydrogen phosphate, dihydrogen phosphate, alkyl guanidino, aryl guanidino, alkyl aryl guanidino, alkyl carbamate, aryl carbamate, alkyl aryl carbamate, alkyl thiocarbamate aryl thiocarbamate, alkyl aryl thiocarbamate, alkyl dithiocarbamate, aryl dithiocarbamate, alkyl aryl dithiocarbamate, bicarbonate, carbonate, perchlorate, chlorate, chlorite, hypochlorite, perbromate, bromate, bromite, hypobromite, tetrahalomanganate, tetrafluoroborate, hexafluorophosphate, hexafluoroantimonate, hypophosphite, iodate, periodate, metaborate, tetraaryl borate, tetra alkyl borate, tartrate, salicylate, succinate, citrate, ascorbate, saccharinate, amino acid, hydroxamic acid, thiotosylate, and anions of ion exchange resins, or systems where one or more of X,Y and Z are independently attached to one or more of the "R" groups, wherein n is 0 or 1. The preferred ligands from which X, Y and Z are selected include halide, organic acid, nitrate and bicarbonate anions.

Currently, the preferred compounds are those wherein at least one pair of "R" groups on adjacent carbon atoms of the macrocycle selected from the group consisting of $R_9$ or $R'_9$ and R or R', $R_1$ or $R'_1$ and $R_2$ or $R'_2$, $R_3$ or $R'_3$ and $R_4$ or $R'_4$, $R_5$ or $R'_5$ and $R_6$ or $R'_6$, and $R_7$ or $R'_7$ and $R_8$ or $R'_8$ are substituted alkyl, substituted alkenyl, substituted alkynyl, substituted cycloalkyl or substituted cycloalkenyl radicals wherein the substituents are independently selected from the group consisting of —$OR_{10}$, —$NR_{10}R_{11}$, —$COR_{10}$, —$CO_2R_{10}$, —$CONR_{10}R_{11}$, —O—(—$(CH_2)_a$—O)$_b$—$R_{10}$, —$SR_{10}$, —$SOR_{10}$, —$SO_2R_{10}$, —$SO_2NR_{10}R_{11}$, —$N(OR_{10})(R_{11})$, —$P(O)(OR_{10})(OR_{11})$, —$P(O)(OR_{10})(R_{11})$ and —$OP(O)(OR_{10})(OR_{11})$, more preferably —$OR_{10}$ or —$NR_{10}R_{11}$, and most preferably —$OR_{10}$ and the remaining "R" groups are hydrogen or, optionally, are independently selected from the group consisting of alkyl, alkenyl, alkynyl, cycloalkyl, cycloalkenyl, cycloalkylalkyl, cycloalkylcycloalkyl, cycloalkenylalkyl, alkylcycloalkyl, alkenylcycloalkyl, alkylcycloalkenyl, alkenylcycloalkenyl, heterocyclic, aryl and aralkyl radicals and radicals attached to the α-carbon of α-amino acids; or $R_1$ or $R'_1$ and $R_2$ or $R'_2$, $R_3$ or $R'_3$ and $R_4$ or $R'_4$, $R_5$ or $R'_5$ and $R_6$ or $R'_6$, $R_7$ or $R'_7$ and $R_8$ or $R'_8$, and $R_9$ or $R'_9$ and R or R' together with the carbon atoms to which they are attached independently form a saturated, partially saturated or unsaturated cyclic having 3 to 20 carbon atoms; or R or R' and $R_1$ or $R'_1$, $R_2$ or $R'_2$ and $R_3$ or $R'_3$, $R_4$ or $R'_4$ and $R_5$ or $R'_5$, $R_6$ or $R'_6$ and $R_7$ or $R'_7$, and $R_8$ or $R'_8$ and $R_9$ or $R'_9$ together with the carbon atoms to which they are attached independently form a nitrogen containing heterocycle having 2 to 20 carbon atoms provided that when the nitrogen containing heterocycle is an aromatic heterocycle which does not contain a hydrogen attached to the nitrogen, the hydrogen attached to the nitrogen in said formula, which nitrogen is also in the macrocycle and the R groups attached to the same carbon atoms of the macrocycle are absent; and combinations thereof. Even more preferred are compounds wherein the "R" groups of the at least one pair of "R" groups on adjacent carbon atoms of the macrocycle are substituted alkyl groups, and the substituents are preferably —$OR_{10}$ and more preferably —OH.

Another preferred group of compounds are those wherein at least one pair of "R" groups on adjacent carbon atoms of the macrocycle selected from the group consisting of $R_9$ or $R'_9$ and R or R', $R_1$ or $R'_1$ and $R_2$ or $R'_2$, $R_3$ or $R'_3$ and $R_4$ or $R'_4$, $R_5$ or $R'_5$ and $R_6$ or $R'_6$, and $R_7$ or $R'_7$ and $R_8$ or $R'_8$ are independently selected wherein one "R" group of the pair is an alkyl, alkenyl, alkynyl, cycloalkyl or cycloalkenyl radical and the other "R" group on the adjacent carbon atom of the macrocycle is a substituted alkyl, substituted alkenyl, substituted alkynyl, substituted cycloalkyl or substituted cycloalkenyl radical wherein the substituents are independently selected from the group consisting of —$OR_{10}$, —$NR_{10}R_{11}$, —$COR_{10}$, —$CO_2R_{10}$, —$CONR_{10}R_{11}$, —O—(—$(CH_2)_a$—O$)_b$—$R_{10}$, —$SR_{10}$, —$SOR_{10}$, —$SO_2R_{10}$, —$SO_2NR_{10}R_{11}$, —$N(OR_{10})(R_{11})$, —$P(O)(OR_{10})(OR_{11})$, —$P(O)(OR_{10})(R_{11})$ and —$OP(O)(OR_{10})(OR_{11})$, more preferably —$OR_{10}$ or —$NR_{10}R_{11}$, and most preferably —$OR_{10}$; and the remaining "R" groups are hydrogen or, optionally, are independently selected from the group consisting of alkyl, alkenyl, alkynyl, cycloalkyl, cycloalkenyl, cycloalkylalkyl, cycloalkylcycloalkyl, cycloalkenylalkyl, alkylcycloalkyl, alkenylcycloalkyl, alkylcycloalkenyl, alkenylcycloalkenyl, heterocyclic, aryl and aralkyl radicals and radicals attached to the α-carbon of α-amino acids; or $R_1$ or $R'_1$ and $R_2$ or $R'_2$, $R_3$ or $R'_3$ and $R_4$ or $R'_4$, $R_5$ or $R'_5$ and $R_6$ or $R'_6$, $R_7$ or $R'_7$ and $R_8$ or $R'_8$, and $R_9$ or $R'_9$ and R or R' together with the carbon atoms to which they are attached independently form a saturated, partially saturated or unsaturated cyclic having 3 to 20 carbon atoms; or R or R' and $R_1$ or $R'_1$, $R_2$ or $R'_2$ and $R_3$ or $R'_3$, $R_4$ or $R'_4$ and $R_5$ or $R'_5$, $R_6$ or $R'_6$ and $R_7$ or $R'_7$, and $R_8$ or $R'_8$ and $R_9$ or $R'_9$ together with the carbon atoms to which they are attached independently form a nitrogen containing heterocycle having 2 to 20 carbon atoms provided that when the nitrogen containing heterocycle is an aromatic heterocycle which does not contain a hydrogen attached to the nitrogen, the hydrogen attached to the nitrogen in said formula, which nitrogen is also in the macrocycle and the R groups attached to the same carbon atoms of the macrocycle are absent; and combinations thereof. Even more preferred are compounds wherein one "R" group of the at least one pair of "R" groups on adjacent carbon atoms of the macrocycle is an alkyl group and the other "R" group on the adjacent carbon atom of the macrocycle is a substituted alkyl group, and the substituent on the carbon atom of the at least one pair of "R" groups on adjacent carbon atoms of the macrocycle which is a substituted group is —$OR_{10}$, and more preferably —OH.

As used herein, "R" groups means all of the R groups attached to the carbon atoms of the macrocycle, i.e., R, R', $R_1$, $R'_1$, $R_2$, $R'_2$, $R_3$, $R'_3$, $R_4$, $R'_4$, $R_5$, $R'_5$, $R_6$, $R'_6$, $R_7$, $R'_7$, $R_8$, $R'_8$, $R_9$. Examples of complexes of the invention include, but are not limited to, compounds having the formulas:

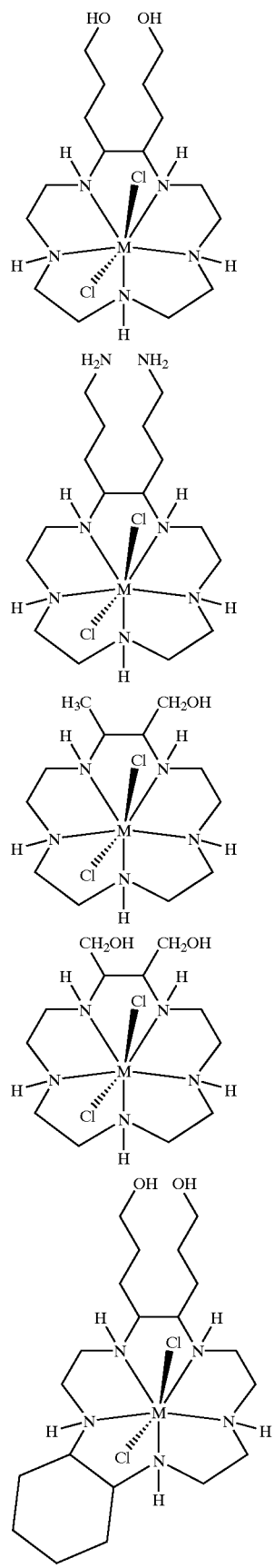

-continued

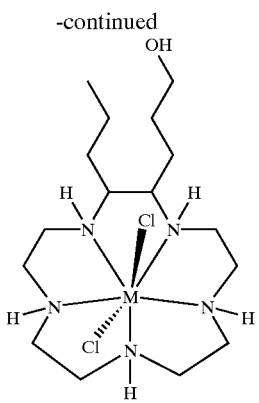

Another embodiment of the invention is a pharmaceutical composition in unit dosage form useful for dismutating superoxide comprising (a) a therapeutically or prophylactically effective amount of a complex as described above and (b) a nontoxic, pharmaceutically acceptable carrier, adjuvant or vehicle.

A further embodiment of the invention is the macrocyclic ligands represented by the formula:

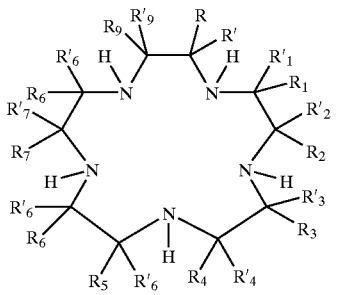

wherein the "R" groups are as defined above.

The commonly accepted mechanism of action of the manganese-based SOD enzymes involves the cycling of the manganese center between the two oxidation states (II,III). See J. V. Bannister, W. H. Bannister, and G. Rotilio, Crit. Rev. Biochem., 22, 111–180 (1987).

Mn(II)+HO$_2$.→Mn(III)+HO$_2$ (1)

Mn(III)+O$_2$.→Mn(II)+O$_2$ (2)

The formal redox potentials for the O$_2$/O$_2$.— and HO$_2$/H$_2$O$_2$ couples at pH=7 are –0.33 v and 0.87 v, respectively. See A. E. G. Cass, in Metalloproteins: Part 1, Metal Proteins with Redox Roles, ed. P. Harrison, P. 121. Verlag Chemie (Weinheim, GDR) (1985). For the above disclosed mechanism, these potentials require that a putative SOD catalyst be able to rapidly undergo oxidation state changes in the range of –0.33 v to 0.87 v.

The complexes derived from Mn(II) and the general class of C-substituted [15]aneN$_5$ ligands described herein have been characterized using cyclic voltammetry to measure their redox potential. The manganese-based C-substituted complexes described herein have reversible oxidations of about +0.7 v (SHE). Coulometry shows that this oxidation is a one-electron process; namely it is the oxidation of the Mn(II) complex to the Mn(III) complex. Thus, for these complexes to function as SOD catalysts, the Mn(III) oxidation state is involved in the catalytic cycle. This means that the Mn(III) complexes of all these ligands are equally competent as SOD catalysts, since it does not matter which form (Mn(II) or Mn(III)) is present when superoxide is present because superoxide will simply reduce Mn(III) to Mn(II) liberating oxygen.

The iron-based complexes of the invention are particularly useful due to the unexpectedly enhanced stability of the iron-based complexes compared to the corresponding manganese-based complexes. The enhanced stability could be important in oral administration and where targeted tissue has very low pH, e.g. ischemic tissue.

As utilized herein, the term "alkyl", alone or in combination, means a straight-chain or branched-chain alkyl radical containing from 1 to about 22 carbon atoms, preferably from about 1 to about 18 carbon atoms, and most preferably from about 1 to about 12 carbon atoms which optionally carries one or more substituents selected from (1) —NR$_{30}$R$_{31}$ wherein R$_{30}$ and R$_{31}$ are independently selected from hydrogen, alkyl, aryl or aralkyl; or R$_{30}$ is hydrogen, alkyl, aryl or aralkyl and R$_{31}$ is selected from the group consisting of —NR$_{32}$R$_{33}$, —OH, —OR$_{34}$,

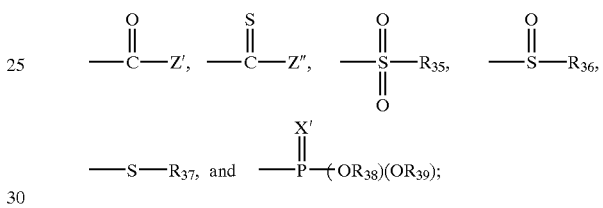

wherein R$_{32}$ and R$_{33}$ are independently hydrogen, alkyl, aryl or acyl, R$_{34}$ is alkyl, aryl or alkaryl, Z' is hydrogen, alkyl, aryl, alkaryl, —OR$_{34}$, —SR$_{34}$ or —NR$_{40}$R$_{41}$ wherein R$_{40}$ and R$_{41}$ are independently selected from hydrogen, alkyl, aryl or alkaryl, Z" is alkyl, aryl, alkaryl, —OR$_{34}$, —SR$_{34}$ or —NR$_{40}$R$_{41}$, R$_{35}$ is alkyl, aryl, —OR$_{34}$, or —NR$_{40}$R$_{41}$, R$_{36}$ is alkyl, aryl or —NR$_{40}$R$_{41}$, R$_{37}$ is alkyl, aryl or alkaryl, X' is oxygen or sulfur, and R$_{38}$ and R$_{39}$ are independently selected from hydrogen, alkyl or aryl; (2) —SR$_{42}$ wherein R$_{42}$ is hydrogen, alkyl, aryl, alkaryl, —SR$_{34}$, —NR$_{32}$R$_{33}$,

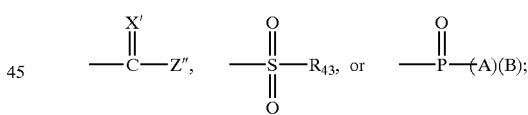

wherein R$_{43}$ is —OH, —OR$_{34}$ or —NR$_{32}$R$_{33}$, and A and B are independently —OR$_{34}$, —SR$_{34}$ or —NR$_{32}$R$_{33}$;

(3)

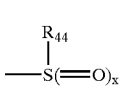

wherein x is 1 or 2, and R$_{44}$ is alkyl, aryl, alkaryl, —OH, —OR$_{34}$, —SR$_{34}$ or —NR$_{32}$R$_{33}$; (4) —OR$_{45}$ wherein R$_{45}$ is hydrogen, alkyl, aryl, alkaryl, —NR$_{32}$R$_{33}$,

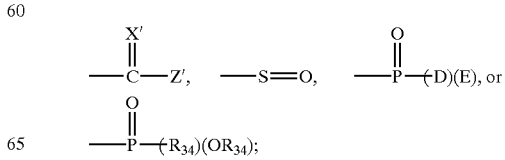

wherein D and E are independently —OR$_{34}$ or —NR$_{32}$R$_{33}$;

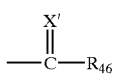
(5)

wherein R$_{46}$ is —OH, —SH, —OR$_{34}$, —SR$_{34}$ or —NR$_{32}$R$_{33}$; or (6) amine oxides of the formula

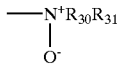

provided R$_{30}$ and R$_{31}$ are not hydrogen; or

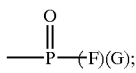
(7)

wherein F and G are independently —OH, —SH, —OR$_{34}$, —SR$_{34}$ or —NR$_{32}$R$_{33}$; or (8) halogen, cyano, nitro, or azido. Alkyl, aryl and alkaryl groups on the substituents of the above-defined alkyl groups may contain one additional substituent but are preferably unsubstituted. Examples of such radicals include, but are not limited to, methyl, ethyl, n-propyl, isopropyl, n-butyl, isobutyl, sec-butyl, tert-butyl, pentyl, isoamyl, hexyl, octyl, nonyl, decyl, dodecyl, tetradecyl, hexadecyl, octadecyl and eicosyl. The term "alkenyl", alone or in combination, means an alkyl radical having one or more double bonds. Examples of such alkenyl radicals include, but are not limited to, ethenyl, propenyl, 1-butenyl, cis-2-butenyl, trans-2-butenyl, iso-butylenyl, cis-2-pentenyl, trans-2-pentenyl, 3-methyl-1-butenyl, 2,3-dimethyl-2-butenyl, 1-pentenyl, 1-hexenyl, 1-octenyl, decenyl, dodecenyl, tetradecenyl, hexadecenyl, cis- and trans-9-octadecenyl, 1,3-pentadienyl, 2,4-pentadienyl, 2,3-pentadienyl, 1,3-hexadienyl, 2,4-hexadienyl, 5,8,11,14-eicosatetraenyl, and 9,12,15-octadecatrienyl. The term "alkynyl", alone or in combination, means an alkyl radical having one or more triple bonds. Examples of such alkynyl groups include, but are not limited to, ethynyl, propynyl (propargyl), 1-butynyl, 1-octynyl, 9-octadecynyl, 1,3-pentadiynyl, 2,4-pentadiynyl, 1,3-hexadiynyl, and 2,4-hexadiynyl. The term "cycloalkyl", alone or in combination means a cycloalkyl radical containing from 3 to about 10, preferably from 3 to about 8, and most preferably from 3 to about 6, carbon atoms. Examples of such cycloalkyl radicals include, but are not limited to, cyclopropyl, cyclobutyl, cyclopentyl, cyclohexyl, cycloheptyl, cyclooctyl, and perhydronaphthyl. The term "cycloalkylalkyl" means an alkyl radical as defined above which is substituted by a cycloalkyl radical as defined above. Examples of cycloalkylalkyl radicals include, but are not limited to, cyclohexylmethyl, cyclopentylmethyl, (4-isopropylcyclohexyl)methyl, (4-t-butyl-cyclohexyl)methyl, 3-cyclohexylpropyl, 2-cyclohexylmethylpentyl, 3-cyclopentylmethylhexyl, 1-(4-neopentylcyclohexyl)methylhexyl, and 1-(4-isopropylcyclohexyl)methylheptyl. The term "cycloalkylcycloalkyl" means a cycloalkyl radical as defined above which is substituted by another cycloalkyl radical as defined above. Examples of cycloalkylcycloalkyl radicals include, but are not limited to, cyclohexylcyclopentyl and cyclohexylcyclohexyl. The term "cycloalkenyl", alone or in combination, means a cycloalkyl radical having one or more double bonds. Examples of cycloalkenyl radicals include, but are not limited to, cyclopentenyl, cyclohexenyl, cyclooctenyl, cyclopentadienyl, cyclohexadienyl and cyclooctadienyl. The term "cycloalkenylalkyl" means an alkyl radical as defined above which is substituted by a cycloalkenyl radical as defined above. Examples of cycloalkenylalkyl radicals include, but are not limited to, 2-cyclohexen-1-ylmethyl, 1-cyclopenten-1-ylmethyl, 2-(1-cyclohexen-1-yl)ethyl, 3-(1-cyclopenten-1-yl)propyl, 1-(1-cyclohexen-1-ylmethyl)pentyl, 1-(1-cyclopenten-1-yl) hexyl, 6-(1-cyclohexen-1-yl)hexyl, 1-(1-cyclopenten-1-yl) nonyl and 1-(1-cyclohexen-1-yl)nonyl. The terms "alkylcycloalkyl" and "alkenylcycloalkyl" mean a cycloalkyl radical as defined above which is substituted by an alkyl or alkenyl radical as defined above. Examples of alkylcycloalkyl and alkenylcycloalkyl radicals include, but are not limited to, 2-ethylcyclobutyl, 1-methylcyclopentyl, 1-hexylcyclopentyl, 1-methylcyclohexyl, 1-(9-octadecenyl) cyclopentyl and 1-(9-octadecenyl)cyclohexyl. The terms "alkylcycloalkenyl" and "alkenylcycloalkenyl" means a cycloalkenyl radical as defined above which is substituted by an alkyl or alkenyl radical as defined above. Examples of alkylcycloalkenyl and alkenylcycloalkenyl radicals include, but are not limited to, 1-methyl-2-cyclopentyl, 1-hexyl-2-cyclopentenyl, 1-ethyl-2-cyclohexenyl, 1-butyl-2-cyclohexenyl, 1-(9-octadecenyl)-2-cyclohexenyl and 1-(2-pentenyl)-2-cyclohexenyl. The term "aryl", alone or in combination, means a phenyl or naphthyl radical which optionally carries one or more substituents selected from alkyl, cycloalkyl, cycloalkenyl, aryl, heterocycle, alkoxyaryl, alkaryl, alkoxy, halogen, hydroxy, amine, cyano, nitro, alkylthio, phenoxy, ether, trifluoromethyl and the like, such as phenyl, p-tolyl, 4-methoxyphenyl, 4-(tert-butoxy) phenyl, 4-fluorophenyl, 4-chlorophenyl, 4-hydroxyphenyl, 1-naphthyl, 2-naphthyl, and the like. The term "aralkyl", alone or in combination, means an alkyl or cycloalkyl radical as defined above in which one hydrogen atom is replaced by an aryl radical as defined above, such as benzyl, 2-phenylethyl, and the like. The term "heterocyclic" means ring structures containing at least one other kind of atom, in addition to carbon, in the ring. The most common of the other kinds of atoms include nitrogen, oxygen and sulfur. Examples of heterocyclics include, but are not limited to, pyrrolidinyl, piperidyl, imidazolidinyl, tetrahydrofuryl, tetrahydrothienyl, furyl, thienyl, pyridyl, quinolyl, isoquinolyl, pyridazinyl, pyrazinyl, indolyl, imidazolyl, oxazolyl, thiazolyl, pyrazolyl, pyridinyl, benzoxadiazolyl, benzothiadiazolyl, triazolyl and tetrazolyl groups. The term "saturated, partially saturated or unsaturated cyclic" means fused ring structures in which 2 carbons of the ring are also part of the fifteen-membered macrocyclic ligand. The ring structure can contain 3 to 20 carbon atoms, preferably 5 to 10 carbon atoms, and can also contain one or more other kinds of atoms in addition to carbon. The most common of the other kinds of atoms include nitrogen, oxygen and sulfur. The ring structure can also contain more than one ring. The term "saturated, partially saturated or unsaturated ring structure" means a ring structure in which one carbon of the ring is also part of the fifteen-membered macrocyclic ligand. The ring structure can contain 3 to 20, preferably 5 to 10, carbon atoms and can also contain nitrogen, oxygen and/or sulfur atoms. The term "nitrogen containing heterocycle" means ring structures in which 2 carbons and a nitrogen of the ring are also part of the fifteen-membered macrocyclic ligand. The ring structure can contain 2 to 20, preferably 4 to 10, carbon atoms, can be partially or fully unsaturated or saturated and can also contain nitrogen, oxygen and/or sulfur atoms in the portion of the ring which is not also part of the fifteen-membered macrocyclic ligand. The term "organic acid anion" refers to carboxylic acid anions having from about 1 to about 18 carbon atoms. The term "halide" means chloride or bromide.

The macrocyclic ligands useful in the complexes of the present invention can also be prepared according to the general procedure shown in Scheme A set forth below. Thus, an amino acid amide, which is the corresponding amide derivative of a naturally or non-naturally occurring α-amino acid, is reduced to form the corresponding substituted ethylenediamine. Such amino acid amide can be the amide derivative of any one of many well known amino acids. Preferred amino acid amides are those represented by the formula:

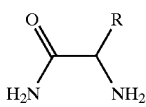

wherein R is derived from the D or L forms of the amino acids Alanine, Aspartic acid, Arginine, Asparagine, Cysteine, Glycine, Glutamic acid, Glutamine, Histidine, Isoleucine, Leucine, Lysine, Methionine, Proline, Phenylalanine, Serine, Tryptophan, Threonine, Tyrosine, Valine and/or the R groups of unnatural α-amino acids such as alkyl, ethyl, butyl, tert-butyl, cycloalkyl, phenyl, alkenyl, allyl, alkynyl, aryl, heteroaryl, polycycloalkyl, polycycloaryl, polycycloheteroaryl, imines, aminoalkyl, hydroxyalkyl, hydroxyl, phenol, amine oxides, thioalkyl, carboalkoxyalkyl, carboxylic acids and their derivatives, keto, ether, aldehyde, amine, nitrile, halo, thiol, sulfoxide, sulfone, sulfonic acid, sulfide, disulfide, phosphonic acid, phosphinic acid, phosphine oxides, sulfonamides, amides, amino acids, peptides, proteins, carbohydrates, nucleic acids, fatty acids, lipids, nitro, hydroxylamines, hydroxamic acids, thiocarbonyls, borates, boranes, boraza, silyl, siloxy, silaza, and combinations thereof. Most preferred are those wherein R represents hydrogen, alkyl, cycloalkylalkyl, and aralkyl radicals. The diamine is then tosylated to produce the di-N-tosyl derivative which is reacted with a di-o-tosylated tris-N-tosylated triazaalkane diol to produce the corresponding substituted N-pentatosylpentaazacycloalkane. The tosyl groups are then removed and the resulting compound is reacted with a manganese(II) or iron (III) compound under essentially anhydrous and anaerobic conditions to form the corresponding substituted manganese(II) or iron (III) pentaazacycloalkane complex. When the ligands or charge-neutralizing anions, i.e. X, Y and Z, are anions or ligands that cannot be introduced directly from the manganese or iron compound, the complex with those anions or ligands can be formed by conducting an exchange reaction with a complex that has been prepared by reacting the macrocycle with a manganese or iron compound.

The complexes of the present invention, wherein $R_9$, and $R_2$ are alkyl, and $R_3$, $R'_3$, $R_4$, $R'_4$, $R_5$, $R'_5$, $R_6$, $R'_6$, $R_7$, $R'_7$, $R_8$ and $R'_8$ can be alkyl, arylalkyl or cycloalkylalkyl and R or R' and $R_1$ or $R'_1$ together with the carbon atoms they are attached to are bound to form a nitrogen containing heterocycle, can also be prepared according to the general procedure shown in Scheme B set forth below utilizing methods known in the art for preparing the manganese(II) or iron (III) pentaazabicyclo[12.3.1]octadecapentaene complex precursor. See, for example, Alexander et al., Inorg. Nucl. Chem. Lett., 6, 445 (1970). Thus a 2,6-diketopyridine is condensed with triethylene tetraamine in the presence of a manganese(II) or iron (III) compound to produce the manganese(II) or iron (III) pentaazabicyclo[12.3.1] octadecapentaene complex. manganese(II) or iron (III) pentaazabicyclo[12.3.1]octadecapentaene complex is hydrogenated with platinum oxide at a pressure of 10–1000 psi to give the corresponding manganese(II) or iron (III) pentaazabicyclo[12.3.1]octadecatriene complex.

The macrocyclic ligands useful in the complexes of the present invention can also be prepared by the diacid dichloride route shown in Scheme C set forth below. Thus, a triazaalkane is tosylated in a suitable solvent system to produce the corresponding tris (N-tosyl) derivative. Such a derivative is treated with a suitable base to produce the corresponding disulfonamide anion. The disulfonamide anion is dialkylated with a suitable electrophile to produce a derivative of a dicarboxylic acid. This derivative of a dicarboxylic acid is treated to produce the dicarboxylic acid, which is then treated with a suitable reagent to form the diacid dichloride. The desired vicinal diamine is obtained in any of several ways. One way which is useful is the preparation from an aldehyde by reaction with cyanide in the presence of ammonium chloride followed by treatment with acid to produce the alpha ammonium nitrile. The latter compound is reduced in the presence of acid and then treated with a suitable base to produce the vicinal diamine. Condensation of the diacid dichloride with the vicinal diamine in the presence of a suitable base forms the tris(tosyl)diamide macrocycle. The tosyl groups are removed and the amides are reduced and the resulting compound is reacted with a manganese (II) or iron (III) compound under essentially anhydrous and anaerobic conditions to form the corresponding substituted pentaazacycloalkane manganese (II) or iron (III) complex.

The vicinal diamines have been prepared by the route shown (known as the Strecker synthesis) and vicinal diamines were purchased when commercially available. Any method of vicinal diamine preparation could be used.

The macrocyclic ligands useful in the complexes of the present invention can also be prepared by the pyridine diamide route shown in Scheme D as set forth below. Thus, a polyamine, such as a tetraaza compound, containing two primary amines is condensed with dimethyl 2,6-pyridine dicarboxylate by heating in an appropriate solvent, e.g., methanol, to produce a macrocycle incorporating the pyridine ring as the 2,6-dicarboxamide. The pyridine ring in the macrocycle is reduced to the corresponding piperidine ring in the macrocycle, and then the diamides are reduced and the resulting compound is reacted with a manganese (II) or iron (III) compound under essentially anhydrous and anaerobic conditions to form the corresponding substituted pentaazacycloalkane manganese (II) or iron (III) complex.

The macrocyclic ligands useful in the complexes of the present invention can also be prepared by the bis (haloacetamide) route shown in Scheme E set forth below. Thus a triazaalkane is tosylated in a suitable solvent system to produce the corresponding tris (N-tosyl) derivative. Such a derivative is treated with a suitable base to produce the corresponding disulfonamide anion. A bis(haloacetamide), e.g., a bis(chloroacetamide), of a vicinal diamine is prepared by reaction of the diamine with an excess of haloacetyl halide, e.g., chloroacetyl chloride, in the presence of a base. The disulfonamide anion of the tris(N-tosyl) triazaalkane is then reacted with the bis(chloroacetamide) of the diamine to produce the substituted tris(N-tosyl)diamide macrocycle. The tosyl groups are removed and the amides are reduced and the resulting compound is reacted with a manganese (II) or iron (III) compound under essentially anhydrous and anaerobic conditions to form the corresponding substituted pentaazacycloalkane manganese (II) or iron (III) complex.

The macrocyclic ligands useful in the complexes of the present invention, wherein $R_1$, $R'_1$, $R_2$, $R'_2$ are derived from a diamino starting material and $R_5$, $R'_5$, $R_7$, $R'_7$ and $R_9$, $R'_9$ can be H or any functionality previously described, can be prepared according to the pseudo-peptide method shown in Scheme F set forth below. A substituted 1,2-diaminoethane represented by the formula

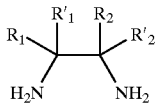

wherein $R_1$, $R'_1$, $R_2$ and $R'_2$ are the substituents on adjacent carbon atoms in the product macrocyclic ligand as set forth above, can be used in this method in combination with any amino acids. The diamine can be produced by any conventional method known to those skilled in the art. The R groups in the macrocycle derived from substituents on the α-carbon of α-amino acids, i.e. $R_5$, $R'_5$, $R_7$, $R'_7$, $R_9$ and $R'_9$, could be derived from the D or L forms of the amino acids Alanine, Aspartic acid, Arginine, Asparagine, Cysteine, Glycine, Glutamic acid, Glutamine, Histidine, Isoleucine, Leucine, Lysine, Methionine, Proline, Phenylalanine, Serine, Tryptophan, Threonine, Tyrosine, Valine and/or the R groups of unnatural α-amino acids such as alkyl, ethyl, butyl, tert-butyl, cycloalkyl, phenyl, alkenyl, allyl, alkynyl, aryl, heteroaryl, polycycloalkyl, polycycloaryl, polycycloheteroaryl, imines, aminoalkyl, hydroxyalkyl, hydroxyl, phenol, amine oxides, thioalkyl, carboalkoxyalkyl, carboxylic acids and their derivatives, keto, ether, aldehyde, amine, nitrile, halo, thiol, sulfoxide, sulfone, sulfonic acid, sulfide, disulfide, phosphonic acid, phosphinic acid, phosphine oxides, sulfonamides, amides, amino acids, peptides, proteins, carbohydrates, nucleic acids, fatty acids, lipids, nitro, hydroxylamines, hydroxamic acids, thiocarbonyls, borates, boranes, boraza, silyl, siloxy, silaza, and combinations thereof. As an example 1,8-dihydroxy, 4,5-diaminooctane is monotosylated and reacted with Boc anhydride to afford the differentiated N-Boc, N-tosyl derivative. The sulfonamide was alkylated with methyl bromoacetate using sodium hydride as the base and saponified to the free acid. The diamine containing N-tosylglycine serves as a dipeptide surrogate in standard solution-phase peptide synthesis. Thus, coupling with a functionalized amino acid ester affords the corresponding pseudo-tripeptide. Two sequential TFA cleavage-couplings affords the pseudo-pentapeptide which can be N- and C-terminus deprotected in one step using HCl/AcOH. DPPA mediated cyclization followed by LiAlH$_4$ or Borane reduction affords the corresponding macrocylic ligand. This ligand system is reacted with a manganese (II) or iron (III) compound, such as manganese (II) chloride or iron (III) chloride, under essentially anaerobic conditions to form the corresponding functionalized manganese (II) or iron (III) pentaazacycloalkane complex. When the ligands or charge-neutralizing anions, i.e. X, Y and Z, are anions or ligands that cannot be introduced directly from the manganese or iron compound, the complex with those anions or ligands can be formed by conducting an exchange reaction with a complex that has been prepared by reacting the macrocycle with a manganese or iron compound.

The following schemes are depicted for preparing the manganese complexes of the invention. The iron complexes of the invention can be prepared by substituting an iron compound for the manganese compound used.

SCHEME A

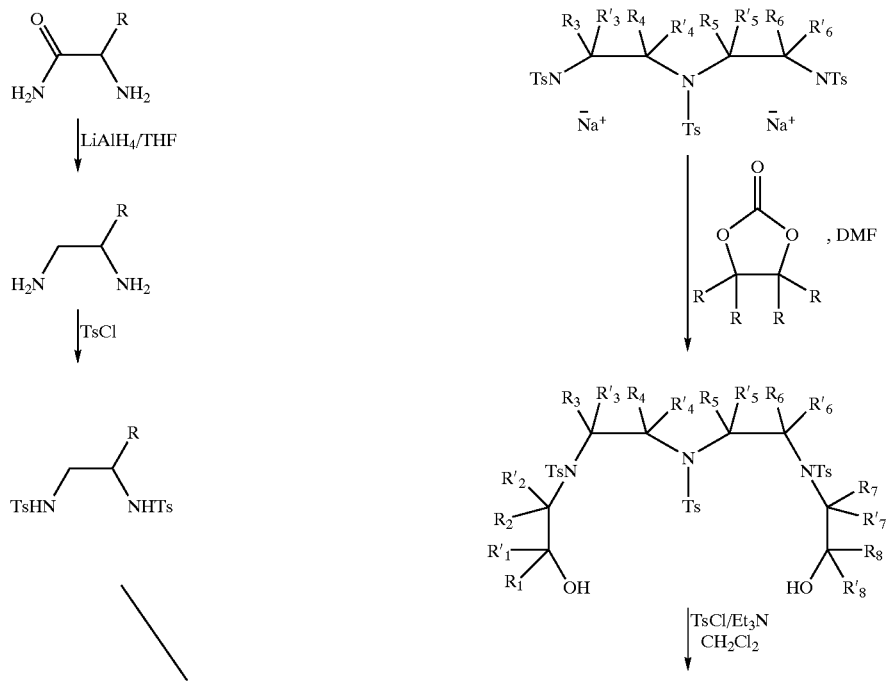

-continued
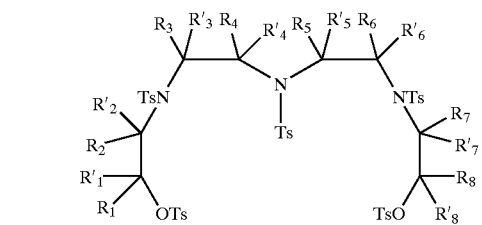
↓ NaH/DMF, 100° C.
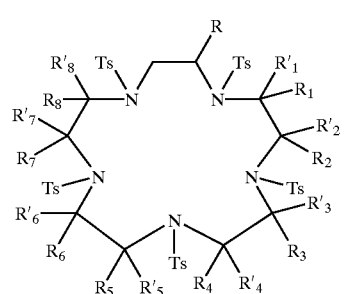
1. HBr or H₂SO₄ or Na⁺[C₁₀H₈]⁻
2. NaOH
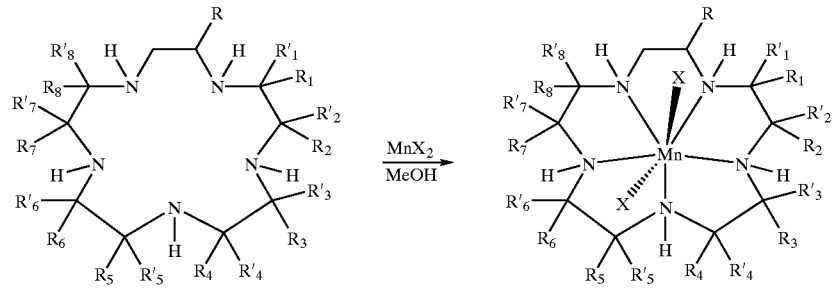
$\xrightarrow{\text{MnX}_2 / \text{MeOH}}$
SCHEME B
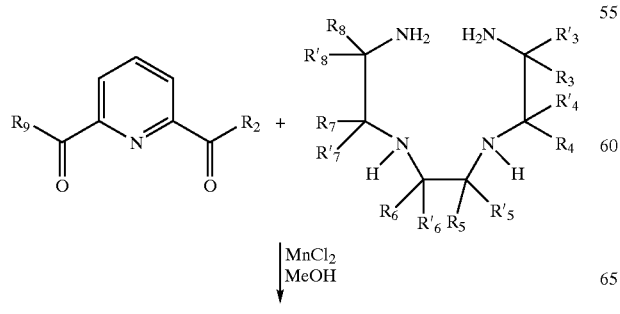
$\Big\downarrow \begin{array}{c} \text{MnCl}_2 \\ \text{MeOH} \end{array}$
-continued
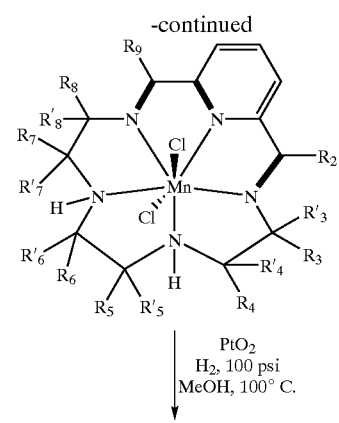
↓ PtO₂, H₂, 100 psi, MeOH, 100° C.

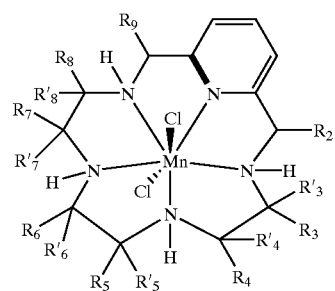
SCHEME C
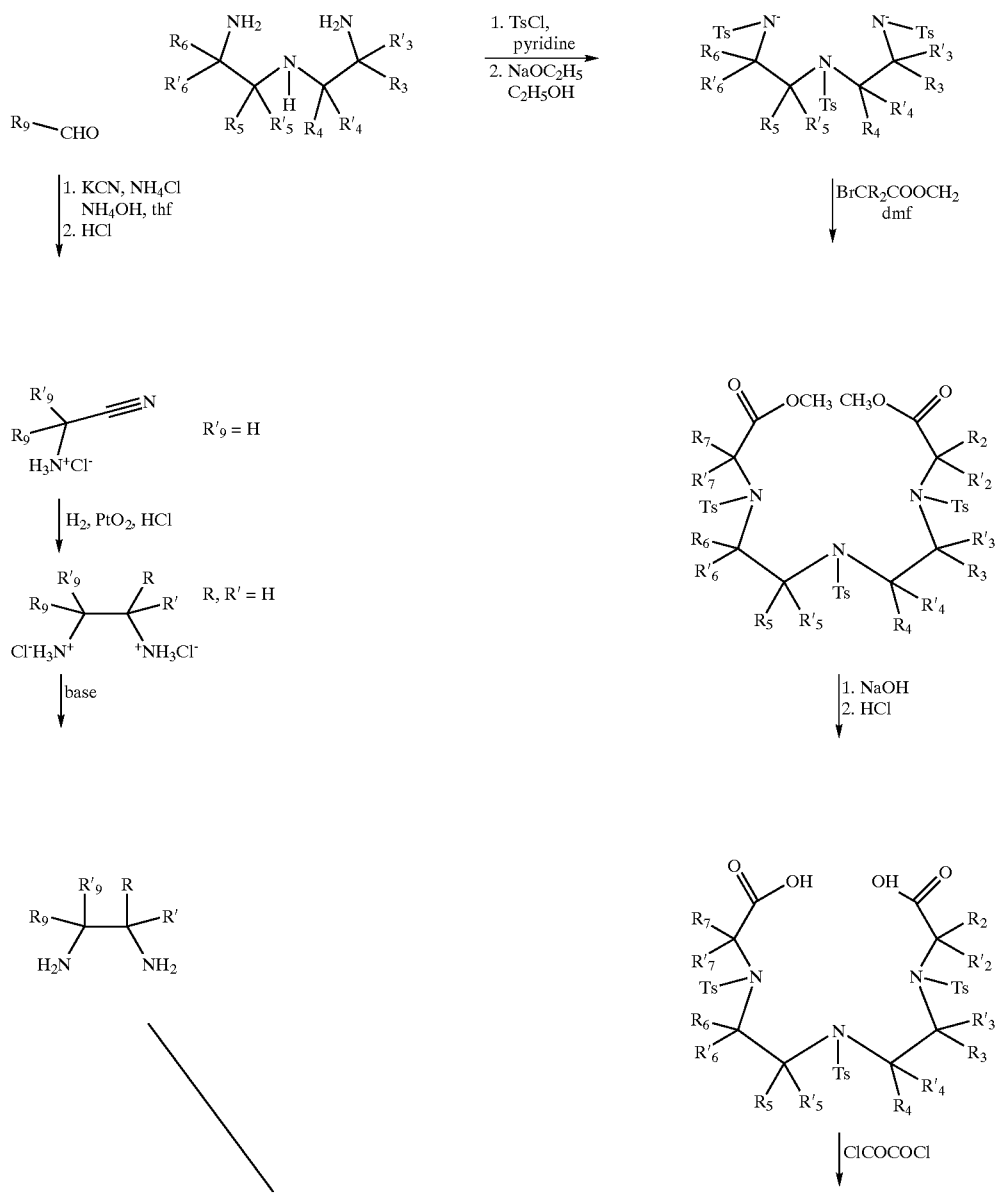

19
20
-continued
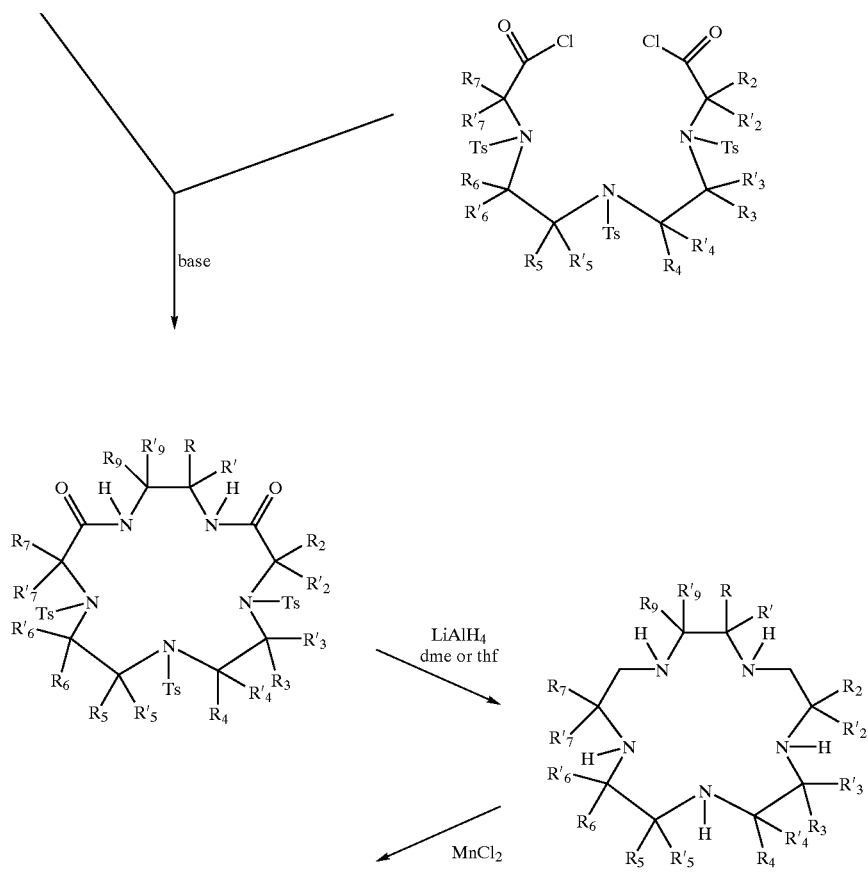
Scheme D
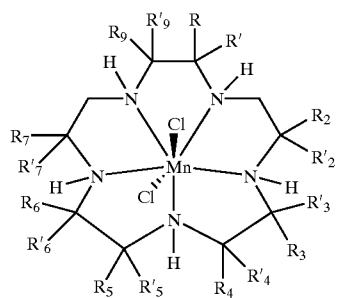
+
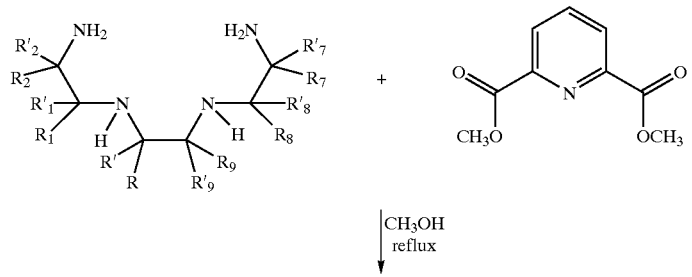
CH₃OH
reflux

-continued
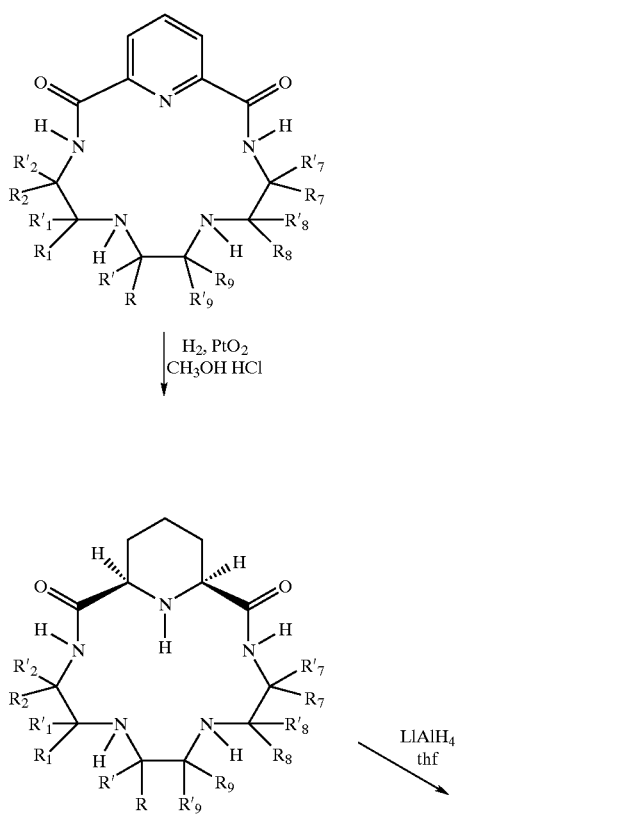
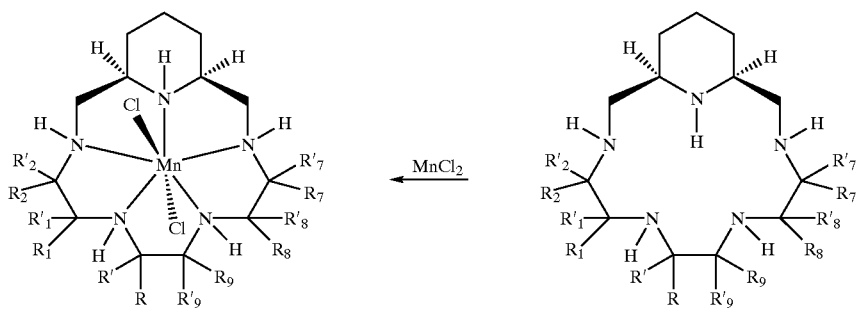
Scheme E
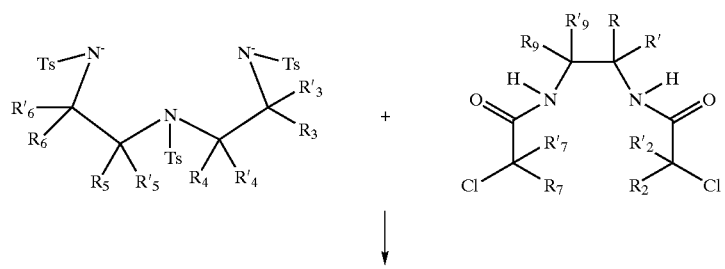

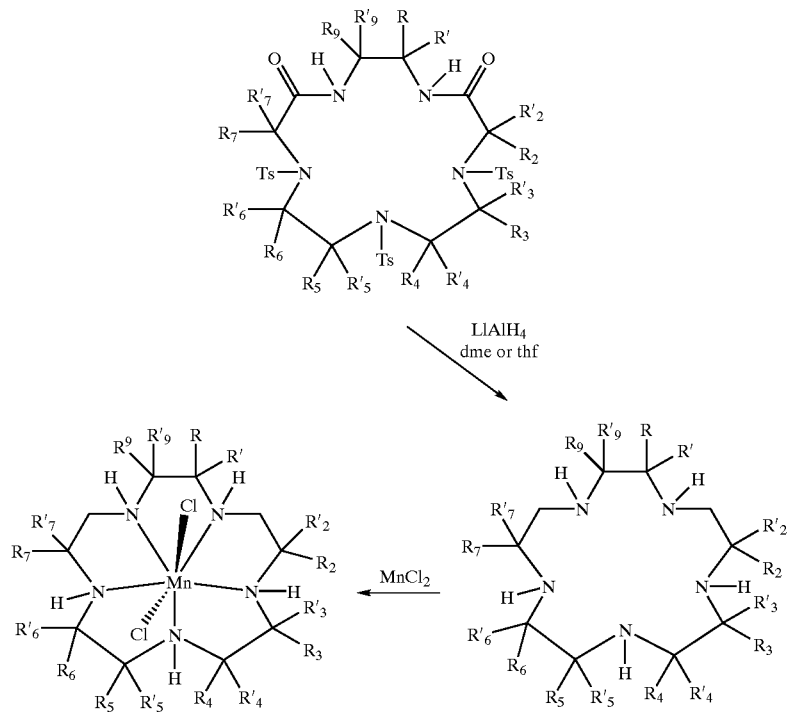
SCHEME F
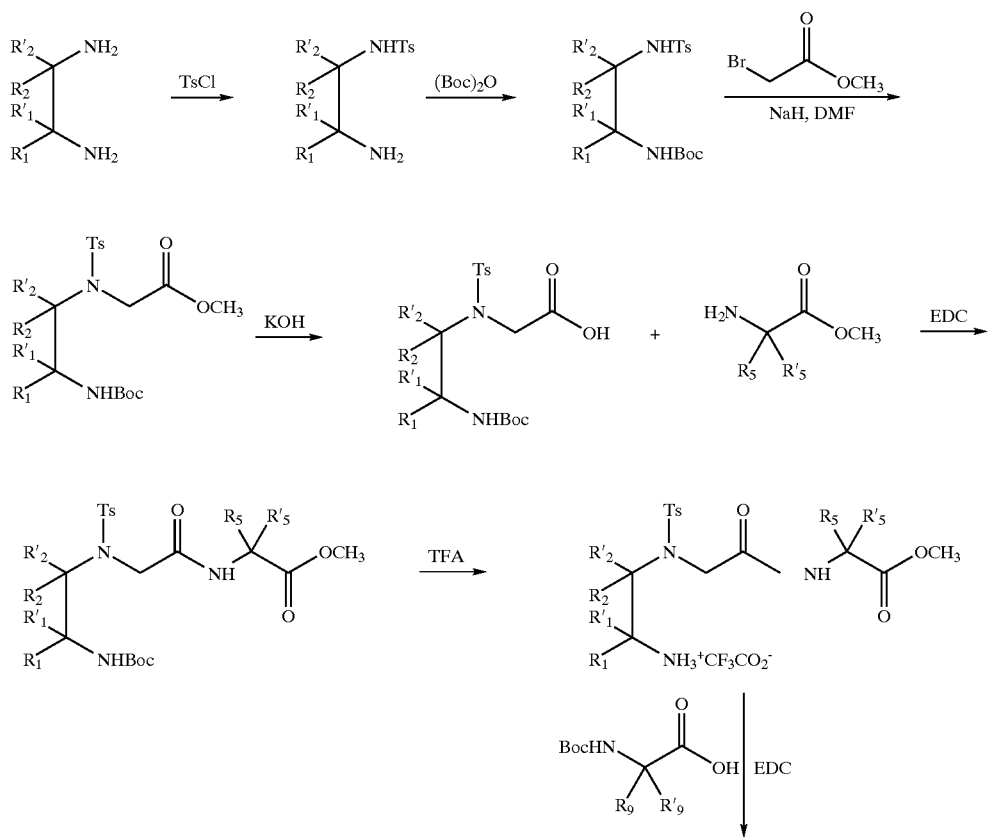

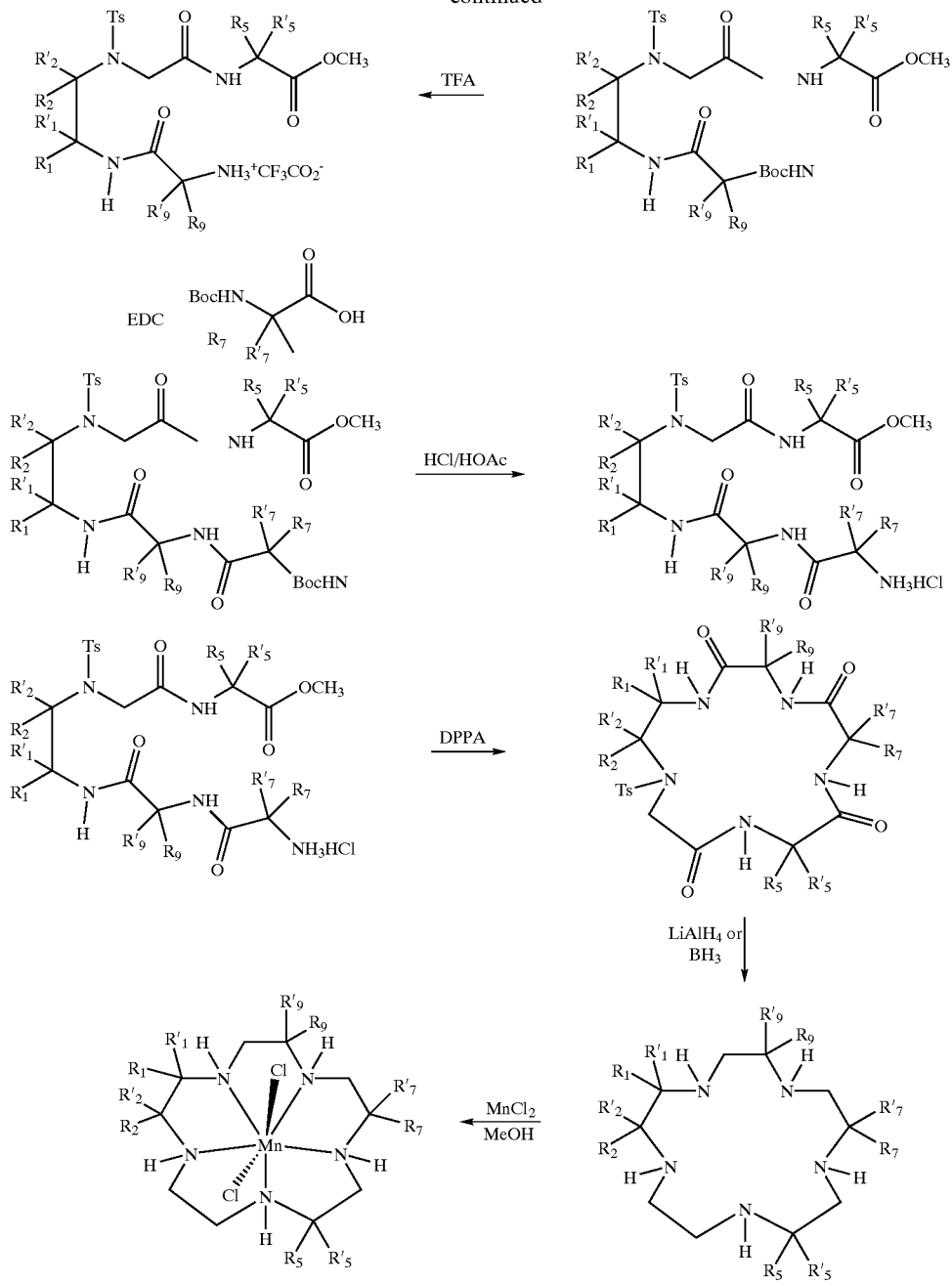

The pentaazamacrocycles of the present invention can possess one or more asymmetric carbon atoms and are thus capable of existing in the form of optical isomers as well as in the form of racemic or nonracemic mixtures thereof. The optical isomers can be obtained by resolution of the racemic mixtures according to conventional processes, for example by formation of diastereoisomeric salts by treatment with an optically active acid. Examples of appropriate acids are tartaric, diacetyltartaric, dibenzoyltartaric, ditoluoyltartaric and camphorsulfonic acid and then separation of the mixture of diastereoisomers by crystallization followed by liberation of the optically active bases from these salts. A different process for separation of optical isomers involves the use of a chiral chromatography column optimally chosen to maximize the separation of the enantiomers. Still another available method involves synthesis of covalent diastereoisomeric molecules by reacting one or more secondary amine group(s) of the compounds of the invention with an optically pure acid in an activated form or an optically pure isocyanate. The synthesized diastereoisomers can be separated by conventional means such as chromatography, distillation, crystallization or sublimation, and then hydrolyzed to deliver the enantiomerically pure ligand. The optically active compounds of the invention can likewise be obtained by utilizing optically active starting materials, such as natural amino acids.

The compounds or complexes of the present invention are novel and can be utilized to treat numerous inflammatory disease states and disorders. For example, reperfusion injury to an ischemic organ, e.g., reperfusion injury to the ischemic myocardium, surgically-induced ischemia, inflammatory bowel disease, rheumatoid arthritis, osteoarthritis, psoriasis, organ transplant rejections, radiation-induced injury, oxidant-induced tissue injuries and damage, atherosclerosis, thrombosis, platelet aggregation, stroke, acute pancreatitis, insulin-dependent diabetes mellitus, disseminated intravascular coagulation, fatty embolism, adult and infantile respiratory distress, metastasis and carcinogenesis.

Activity of the compounds or complexes of the present invention for catalyzing the dismutation of superoxide can be demonstrated using the stopped-flow kinetic analysis technique as described in Riley, D.P., Rivers, W. J. and Weiss, R. H., "Stopped-Flow Kinetic Analysis for Monitoring Superoxide Decay in Aqueous Systems," *Anal. Biochem.*, 196, 344–349 (1991), which is incorporated by reference herein. Stopped-flow kinetic analysis is an accurate and direct method for quantitatively monitoring the decay rates of superoxide in water. The stopped-flow kinetic analysis is suitable for screening compounds for SOD activity and catalytic activity of the compounds or complexes of the present invention for dismutating superoxide, as shown by stopped-flow analysis, correlate to treating the above disease states and disorders.

Total daily dose administered to a host in single or divided doses may be in amounts, for example, from about 1 to about 100 mg/kg body weight daily and more usually about 3 to 30 mg/kg. Unit dosage compositions may contain such amounts of submultiples thereof to make up the daily dose.

The amount of active ingredient that may be combined with the carrier materials to produce a single dosage form will vary depending upon the host treated and the particular mode of administration.

The dosage regimen for treating a disease condition with the compounds and/or compositions of this invention is selected in accordance with a variety of factors, including the type, age, weight, sex, diet and medical condition of the patient, the severity of the disease, the route of administration, pharmacological considerations such as the activity, efficacy, pharmacokinetic and toxicology profiles of the particular compound employed, whether a drug delivery system is utilized and whether the compound is administered as part of a drug combination. Thus, the dosage regimen actually employed may vary widely and therefore may deviate from the preferred dosage regimen set forth above.

The compounds of the present invention may be administered orally, parenterally, by inhalation spray, rectally, or topically in dosage unit formulations containing conventional nontoxic pharmaceutically acceptable carriers, adjuvants, and vehicles as desired. Topical administration may also involve the use of transdermal administration such as transdermal patches or iontophoresis devices. The term parenteral as used herein includes subcutaneous injections, intravenous, intramuscular, intrasternal injection, or infusion techniques.

Injectable preparations, for example, sterile injectable aqueous or oleaginous suspensions may be formulated according to the known art using suitable dispersing or wetting agents and suspending agents. The sterile injectable preparation may also be a sterile injectable solution or suspension in a nontoxic parenterally acceptable diluent or solvent, for example, as a solution in 1,3-butanediol. Among the acceptable vehicles and solvents that may be employed are water, Ringer's solution, and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

Suppositories for rectal administration of the drug can be prepared by mixing the drug with a suitable nonirritating excipient such as cocoa butter and polyethylene glycols which are solid at ordinary temperatures but liquid at the rectal temperature and will therefore melt in the rectum and release the drug.

Solid dosage forms for oral administration may include capsules, tablets, pills, powders, granules and gels. In such solid dosage forms, the active compound may be admixed with at least one inert diluent such as sucrose lactose or starch. Such dosage forms may also comprise, as in normal practice, additional substances other than inert diluents, e.g., lubricating agents such as magnesium stearate. In the case of capsules, tablets, and pills, the dosage forms may also comprise buffering agents. Tablets and pills can additionally be prepared with enteric coatings.

Liquid dosage forms for oral administration may include pharmaceutically acceptable emulsions, solutions, suspensions, syrups, and elixirs containing inert diluents commonly used in the art, such as water. Such compositions may also comprise adjuvants, such as wetting agents, emulsifying and suspending agents, and sweetening, flavoring, and perfuming agents.

While the compounds of the invention can be administered as the sole active pharmaceutical agent, they can also be used in combination with one or more compounds which are known to be effective against the specific disease state that one is targeting for treatment.

The compounds or complexes of the invention can also be utilized as MRI contrast agents. A discussion of the use of contrast agents in MRI can be found in patent application Ser. No. 08/397,469, which is incorporated by reference herein.

Contemplated equivalents of the general formulas set forth above for the compounds and derivatives as well as the intermediates are compounds otherwise corresponding thereto and having the same general properties such as tautomers of the compounds and such as wherein one or more of the various R groups are simple variations of the substituents as defined therein, e.g., wherein R is a higher alkyl group than that indicated, or where the tosyl groups are other nitrogen or oxygen protecting groups or wherein the O-tosyl is a halide. Anions having a charge other than 1, e.g., carbonate, phosphate, and hydrogen phosphate, can be used instead of anions having a charge of 1, so long as they do not adversely affect the overall activity of the complex. However, using anions having a charge other than 1 will result in a slight modification of the general formula for the complex set forth above. In addition, where a substituent is designated as, or can be, a hydrogen, the exact chemical nature of a substituent which is other than hydrogen at that position, e.g., a hydrocarbyl radical or a halogen, hydroxy, amino and the like functional group, is not critical so long as it does not adversely affect the overall activity and/or synthesis procedure. Further, it is contemplated that manganese(III) and iron (II) complexes will be equivalent to the subject manganese(II) and iron (III) complexes.

The chemical reactions described above are generally disclosed in terms of their broadest application to the preparation of the compounds of this invention. occasionally, the reactions may not be applicable as described to each compound included within the disclosed scope. The compounds for which this occurs will be readily recognized by those skilled in the art. In all such cases, either the reactions can be successfully performed by conventional modifications known to those skilled in the art, e.g., by appropriate protection of interfering groups, by changing to alternative conventional reagents, by routine modification of reaction conditions, and the like, or other reactions disclosed herein or otherwise conventional, will be applicable to the preparation of the corresponding compounds of this invention. In all preparative methods, all starting materials are known or readily preparable from known starting materials.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever.

EXAMPLES

All reagents were used as received without purification unless otherwise indicated. All NMR spectra were obtained on a Varian VXR-300 or VXR-400 nuclear magnetic resonance spectrometer. Qualitative and quantitative mass spectroscopy was run on a Finnigan MAT90, a Finnigan 4500 and a VG40-250T using m-nitrobenzyl alcohol(NBA), m-nitrobenzyl alcohol/LiCl (NBA-Li) or m-nitrobenzyl alcohol (NBA-HC). Melting points (mp) are uncorrected.

The following abbreviations are in accordance with common usage.

| | |
|---|---|
| DMSO | Dimethylsulfoxide |
| THF | Tetrahydrofuran |
| DMF | Dimethylformamide |

Example 1

Synthesis of [Manqanese(II) dichloro (trans-2,3-bis (3-hydroxypropyl)-1,4,7,10,13-pentaazacyclopentadecane)]

1.A. Synthesis of D,L-4,5-Diamino-1,7-octadiene

D,L-4,5-Diamino-1,7-octadiene was prepared according to (1) with the following modifications: D,L-4,5-bis (diphenylmethylamino)-1,7-octadiene (76.2 g, 161 mmol) was dissolved in trifluoroacetic acid (150 ml) under a dry argon atmosphere and triethylsilane (75.0 g, 645 mmol) was then added. The red-brown solution was refluxed for 30 minutes and the solvent was removed in vacuo. The residue was dissolved in 1N HCl (500 ml) and concentrated to a volume of 200 ml in vacuo. Then, 1N HCl (800 ml) was added and the solution was washed with $CH_2Cl_2$ (3×500 ml) and ethyl ether (500 ml). The solvent was removed in vacuo and the crude product was crystallized from methanol-ethyl ether to give 28.1 g (81.9% yield) of the hydrochloride salt as colorless needles: mp 190–3° C.; $^1$H NMR (DMSO-$d_6$, 400 MHz) δ 2.37 (m, 2H), 2.63 (m, 2H), 3.58 (m, 2H), 5.20 (d, J=10.2 Hz, 2H), 5.28 (dd, J=1.47, 18.6 Hz, 2H), 5.79 (m, 2H), 8.65 (br s, 6H); $^{13}$C NMR (DMSO-$d_6$, 100 MHz) δ 31.59, 51.01, 119.71, 132.33; FAB mass spectrum (GT-HCl) m/z 141 [M+H]$^+$.

D, L-4,5-Diamino-1,7-octadiene dihydrochloride (28.0 g, 131 mmol) was slurried in MeOH (50 ml) and a solution of KOH (14.7 g, 262 mmol) in MeOH (30 ml) was added dropwise under an argon atmosphere with stirring. Ethyl ether (1 l) was added and the mixture was then dried with $Na_2SO_4$. The salts were filtered and washed with ethyl ether. The filtrate was concentrated in vacuo to give 17.7 g (95.9% yield) of the diamine as a light yellow liquid: $^1$H NMR (CDCl$_3$, 300 MHz) δ 1.34 (s, 4H), 2.07 (m, 2H), 2.31 (m, 2H), 2.69 (m, 2H), 5.12 (m, 4H), 5.81 (m, 2H); $^{13}$C NMR (CDCl$_3$, 75 MHz) δ 39.68, 54.43, 117.29, 135.98.

References (1) Neumann, W. L., Rogic, M. M. and Dunn, J. T., Tetrahedron Lett., 32, 5865–8 (1991).

1.B. Synthesis of D,L-N,N'-Bis(chloroacetyl)-4,5-diamino-1,7-octadiene

To a stirred solution of D,L-4,5-diamino-1,7-octadiene prepared as in Example 1A (17.5 g, 124 mmol) in alcohol-free CHCl$_3$ (590 ml) was added H$_2$O (120 ml) and the resulting mixture was cooled to 0° C. Solutions of chloroacetyl chloride (43.1 g, 382 mmol) in alcohol-free CHCl$_3$ (235 ml) and K$_2$CO$_3$ (49.3 g, 357 mmol) in H$_2$O (495 ml) were added simultaneously under an argon atmosphere over 1.75 h while maintaining the temperature at 0° C. The mixture was then allowed to warm to room temperature while stirring an additional 2 h. The layers were separated and the aqueous layer was extracted with CHCl$_3$ (1 l). The combined CHCl$_3$ layers were washed with H$_2$O (3×500 ml), saturated NaCl solution and were dried (MgSO$_4$). The solvent was removed in vacuo to give 35.9 g (98.4% yield) of the product as a white crystalline solid: mp 120–2° C.; $^1$H NMR (CDCl$_3$, 400 MHz) δ 2.37 (m, 2H), 2.44 (m, 2H), 4.03 (m, 6H), 5.16 (m, 4H), 5.76 (m, 2H), 6.90 (d, J=5.4 Hz, 2H); $^{13}$C NMR (CDCl$_3$, 100 MHz) δ 36.08, 42.59, 52.33, 119.07, 132.83, 166.68; CI mass spectrum (CH$_4$) m/z 293 [M+H]$^+$.

1.C. Synthesis of D,L-5,6-Bis(2-propenvl)-1,10,13-tris-(p-toluenesulfonyl)-1,4,7,10,13-pentaazacyclopentadecane-3,8-dione A solution of 1,4,7-tris(p-toluenesulfonyl)-1,4,7-triazaheptane-1,7-disodium salt (61.0 g, 100 mmol), prepared according to the procedure described in Example 1 of EP Patent Application 0 524 161 A1, in degassed anhydrous DMF (1 l) and a solution of D,L-N,N'-bis(chloroacetyl)-4,5-diamino-1,7-octadiene (29.3 g, 100 mmol) in degassed anhydrous DMF (1 l) were simultaneously added to degassed anhydrous DMF (4 l) under a dry argon atmosphere at room temperature over 4.5 h. The mixture was then stirred for an additional 18 h at room temperature and the solvent was removed in vacuo. The residue was dissolved in CH$_2$Cl$_2$ (1 l), washed with H$_2$O (2×1 l), saturated NaCl solution (500 ml) and was dried (MgSO$_4$). The solvent was removed in vacuo to give the crude product as a yellow crystalline solid. The solid was dissolved in CH$_2$Cl$_2$ and MeOH (2 l) was added. Crystallization by removal of the CH$_2$Cl$_2$ in vacuo gave 47.7 g (60.7% yield) of the product as colorless needles: mp 180–2° C.; $^1$H NMR (CDCl$_3$, 300 MHz) δ 1.60 (br s, 2H), 2.26 (m, 2H), 2.45 (s, 9H), 3.19 (m, 4H), 3.45 (m, 4H), 3.70 (dd, J=11.6, 16.1 Hz, 4H), 4.01 (m, 2H), 5.16 (s, 2H), 5.21 (d, J=6.1 Hz, 2H), 5.75 (m, 2H), 6.55 (d, J=7.3 Hz, 2H), 7.33 (m, 6H), 7.70 (m, 6H); $^{13}$C NMR (CDCl$_3$, 100 MHz) δ 21.58, 36.00, 49.63, 51.50, 51.71, 54.33, 119.63, 127.51, 127.69, 129.95, 130.09, 132.14, 133.99, 134.40, 143.92, 144.44, 168.37; FAB mass spectrum (NBA-Li) 792.2 [M+Li]$^+$.

1.D Synthesis of D,L-5,6-Bis(3-hydroxypropyl)-1,10,13-tris-(p-toluenesulfonyl)-1,4,7,10,13-entaazacyclopentadecane-3,8-dione To a stirred suspension of D,L-5,6-bis(2-propenyl)-1,10,13-tris-(p-toluenesulfonyl)-1,4,7,10,13-pentaazacyclopentadecane-3,8-dione (20.0 g, 25.5 mmole), prepared as in Example 1C, in anhydrous THF (300 ml) under a dry argon atmosphere was added a solution of borane in THF (63.6 ml–1.0 M, 63.6 mmole) dropwise over 30 Thin at 0° C. The solid had dissolved by the end of the addition and stirring was continued at 0° C. for another 3 h. Water (10 ml) was then added to destroy excess borohydride and 3 M NaOH (21.2 ml) was then added also at 0° C. Then 30% H$_2$O$_2$ (7.23 ml) was added at 0° C. and the resulting colorless solution was allowed to warm to room temperature while stirring for another 30 min. Saturated NaCl solution (200 ml) was added to the solution and the product was extracted with ethyl ether (2×500 ml). The organic layers were combined and washed with saturated NaCl solution (2×100 ml). Product had begun to crystallize from the ether solution. The solvent was removed in vacuo to give a crystalline solid. Crystallization from MeOH—ethyl ether gave 18.2 g (87.0%) of the product containing secondary alcohol byproduct. Recrystallization of this from $CHCl_3$—ethyl ether gave 13.8 g (65.9%) of the product as colorless needles: mp 220–2° C.; $^1H$ NMR ($CDCl_3$, 300 MHz) δ 1.62 (m, 6H), 1.80 (m, 2H), 2.42 (s, 6H), 2.43 (s, 3H), 2.63 (br s, 2H), 3.17 (m, 2H), 3.21 (m, 2H), 3.45 (m, 4H), 3.60 (m, 6H), 3.91 (d, J=17.1 Hz, 2H), 3.97 (m, 2H), 7.15 (d, J=8.3 Hz, 2H), 7.32 (d, J=8.3 Hz, 6H), 7.65 (d, J=8.3 Hz, 2H), 7.71 (d, J=8.3 Hz, 4H); $^{13}C$ NMR ($CDCl_3$, 100 MHz) δ 21.58, 27.96, 28.80, 49.51, 51.56, 52.68, 54.18, 62.09, 127.45, 127.66, 129.94, 130.09, 133.96, 134.44, 143.86, 144.46, 168.73; FAB mass spectrum (NBA-Li) m/z 828 $[M+H]^+$.

1.E. Synthesis of D,L-2,3-Bis(3-hydroxypropyl)-1,4,7,10,13-pentaazacyclopentadecane To a stirred suspension of D,L-5,6-bis(3-hydroxypropyl)-1,10,13-tris(p-toluenesulfonyl)-1,4,7,10,13-pentaazacyclopentadecane-3,8-dione (5.00 g, 6.08 mmole), prepared as in Example 1D, in anhydrous THF (100 ml) under a dry argon atmosphere was added a solution of 1.0 M $LiAlH_4$ in THF (76.0 ml, 76.0 mmole) dropwise over 5 minutes The yellow homogeneous solution was refluxed for 30 h (by which time it had become heterogeneous) and was then cooled to 0° C. The mixture was then quenched by the dropwise addition of saturated $Na_2SO_4$ (15 ml) while cooling in an ice bath. The solvent was removed in vacuo and any remaining water was removed by azeotroping with toluene (3×500 ml) and then hexanes (3×500 ml). The solids were then extracted with refluxing, anhydrous, inhibitor-free THF (2×500 ml and 2×700 ml), filtering the solid each time under an argon atmosphere. The solvent was removed in vacuo from the extracts to give oils which rapidly crystallized. The crude product was purified by crystallization from acetonitrile—ethyl ether to give 500 mg (24.8%) of a colorless crystalline solid: mp 105–6° C.; $^1H$ NMR ($CDCl_3$, 400 MHz) δ 1.59 (m, 4H), 1.70 (m, 4H), 2.73 (m, 25H), 3.51 (m, 2H), 3.66 (m, 2H); $^{13}C$ NMR ($CDCl_3$, 100 MHz) δ 26.85, 27.32, 46.89, 47.97, 48.28, 48.70, 58.17, 62.95; CI mass spectrum ($CH_4$) 332 $[M+H]^+$.

1.F. Synthesis of [Manganese(II) dichloro trans-2,3-bis(3-hydroxypropyl)-1,4,7,10,13-pentaazacyclopentadecane)]

To a stirred solution of anhydrous $MnCl_2$ (126 mg, 1.00 mmole) in methanol was added D,L-2,3-bis(3-hydroxypropyl)-1,4,7,10, 13-pentaazacyclopentadecane prepared as in Example 1E (331 mg, 1.00 mmole) and the solution was refluxed for 2 h and then stirred at room temperature overnight. The solvent was removed in vacuo and the white solid was redissolved in a mixture of THF (20 ml) and ethanol (3 ml) and filtered through Celite™ diatomaceous earth. The filtrate was concentrated to a volume of 3 ml, ethanol (3 ml) was added and the solution was heated to reflux. THF (20 ml) was added to the solution and the crystals which formed were collected to give 820 mg (69%) of the product as a white solid: FAB mass spectrum (NBA-HCl) m/z (relative intensity) 421/423 $[(M-Cl)^+, 100/33]$; Anal. Calcd. For $C_{16}H_{37}N_5MnCl_2$: C, 42.02; H, 8.15; N, 15.31; Cl, 15.50. Found: C, 42.11; H, 8.14; N, 15.29; Cl, 15.59.

Example 2

Stopped-Flow Kinetic Analysis

Stopped-flow kinetic analysis has been utilized to determine whether a compound can catalyze the dismutation of superoxide (Riley, D. P., Rivers, W. J. and Weiss, R. H., "Stopped-Flow Kinetic Analysis for Monitoring Superoxide Decay in Aqueous Systems," Anal. Biochem, 196, 344–349 [1991]). For the attainment of consistent and accurate measurements all reagents were biologically clean and metal-free. To achieve this, all buffers (Calbiochem) were biological grade, metal-free buffers and were handled with utensils which had been washed first with 0.1 N HCl, followed by purified water, followed by a rinse in a $10^4$ M EDTA bath at pH 8, followed by a rinse with purified water and dried at 65° C. for several hours. Dry DMSO solutions of potassium superoxide (Aldrich) were prepared under a dry, inert atmosphere of argon in a Vacuum Atmospheres dry glovebox using dried glassware. The DMSO solutions were prepared immediately before every stopped-flow experiment. A mortar and pestle were used to grind the yellow solid potassium superoxide (~100 mg). The powder was then ground with a few drops of DMSO and the slurry transferred to a flask containing an additional 25 ml of DMSO. The resultant slurry was stirred for 1/2 h and then filtered. This procedure gave reproducibly ~2 mM concentrations of superoxide in DMSO. These solutions were transferred to a glovebag under nitrogen in sealed vials prior to loading the syringe under nitrogen. It should be noted that the DMSO/superoxide solutions are extremely sensitive to water, heat, air, and extraneous metals. A fresh, pure solution has a very slight yellowish tint.

Water for buffer solutions was delivered from an in-house deionized water system to a Barnstead Nanopure Ultrapure Series 550 water system and then double distilled, first from alkaline potassium permanganate and then from a dilute EDTA solution. For example, a solution containing 1.0 g of potassium permanganate, 2 liters of water and additional sodium hydroxide necessary to bring the pH to 9.0 were added to a 2-liter flask fitted with a solvent distillation head. This distillation will oxidize any trace of organic compounds in the water. The final distillation was carried out under nitrogen in a 2.5-liter flask containing 1500 ml of water from the first still and $1.0 \times 10^6$ M EDTA. This step will remove remaining trace metals from the ultrapure water. To prevent EDTA mist from volatilizing over the reflux arm to the still head, the 40-cm vertical arm was packed with glass beads and wrapped with insulation. This system produces deoxygenated water that can be measured to have a conductivity of less than 2.0 nanomhos/$cm^2$.

The stopped-flow spectrometer system was designed and manufactured by Kinetic Instruments Inc. (Ann Arbor, Mich.) and was interfaced to a MAC IICX personal computer. The software for the stopped-flow analysis was provided by Kinetics Instrument Inc. and was written in Quick-Basic with MacAdios drivers. Typical injector volumes (0.10 ml of buffer and 0.006 ml of DMSO) were calibrated so that a large excess of water over the DMSO solution were mixed together. The actual ratio was approximately 19/1 so that the initial concentration of superoxide in the aqueous solution was in the range 60–120 $\mu$M. Since the published extinction coefficient of superoxide in $H_2O$ at 245 nm is ~2250 $M^{-1}$ $cm^{-1}$ (1), an initial absorbance value of approximately 0.3–0.5 would be expected for a 2-cm path length cell, and this was observed experimentally. Aqueous solutions to be mixed with the DMSO solution of superoxide were prepared using 80 mM concentrations of the Hepes buffer, pH 8.1 (free acid+Na form). One of the reservoir syringes was filled with 5 ml of the DMSO solution while the other was filled with 5 ml of the aqueous buffer solution. The entire injection block, mixer, and spectrometer cell were immersed in a thermostatted circulating water bath with a temperature of 21.0±0.5° C.

Prior to initiating data collection for a superoxide decay, a baseline average was obtained by injecting several shots of the buffer and DMSO solutions into the mixing chamber. These shots were averaged and stored as the baseline. The first shots to be collected during a series of runs were with aqueous solutions that did not contain catalyst. This assures that each series of trials were free of contamination capable of generating first-order superoxide decay profiles. If the decays observed for several shots of the buffer solution were second-order, solutions of manganese(II) complexes could be utilized. In general, the potential SOD catalyst was screened over a wide range of concentrations. Since the initial concentration of superoxide upon mixing the DMSO with the aqueous buffer was ~$1.2\times10^{-4}$ M, we wanted to use a manganese (II) complex concentration that was at least 20 times less than the substrate superoxide. Consequently, we generally screened compounds for SOD activity using concentrations ranging from $5\times10^{-7}$ to $8\times10^{-6}$ M. Data acquired from the experiment was imported into a suitable math program (e.g., Cricket Graph) so that standard kinetic data analyses could be performed. The catalytic rate constant for dismutation of superoxide by the manganese(II) complex of Example 1 was determined from the linear plot of observed rate constants ($k_{obs}$) versus the concentration of the manganese(II) complexes. $k_{obs}$ values were obtained from the liner plots of ln absorbance at 245 nm versus time for the dismutation of superoxide by the manganese(II) complex. The $k_{cat}$ ($M^{-1}$ $sec^{-1}$) of the manganese (II) complex of Example 1 at pH=8.1 and 21° C. was determined to be $1.8\times10^{+7}$ $M^{-1}$ $sec^{-1}$.

The manganese(II) complex of the nitrogen-containing macrocyclic ligand in Example 1 is an effective catalyst for the dismutation of superoxide, as can be seen from the $k_{cat}$ above.

What is claimed is:

1. A compound which is a complex represented by the formula:

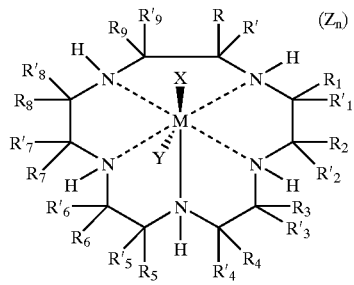

wherein at least one pair of "R" groups on adjacent carbon atoms of the macrocycle selected from the group consisting of $R_9$ or $R'_9$ and R or R', $R_1$ or $R'_1$ and $R_2$ or $R'_2$, $R_3$ or $R'_3$ and $R_4$ or $R'_4$, $R_5$ or $R'_5$ and $R_6$ or $R'_6$, and $R_7$ or $R'_7$ and $R_8$ or $R'_8$ are substituted alkyl substituted alkenyl, substituted alkynyl, substituted cycloalkyl or substituted cycloalkenyl radicals wherein the substituents are independently selected from the group consisting of —$OR_{10}$, —$NR_{10}R_{11}$, —$COR_{10}$, —$CO_2R_{10}$, —$CONR_{10}R_{11}$, —O—(—($CH_2$)$_a$—O)$_b$—$R_{10}$, —$SR_{10}$, —$SOR_{10}$, —$SO_2R_{10}$, —$SO_2NR_{10}R_{11}$, —$N(OR_{10})(R_{11})$, —$P(O)(OR_{10})(OR_{11})$, —$P(O)(OR_{10})(R_{11})$ and —$OP(O)(OR_{10})(OR_{11})$; or at least one pair of "R" groups on adjacent carbon atoms of the macrocycle selected from the group consisting of $R_9$ or $R'_9$ and R or R', $R_1$ or $R'_1$ and $R_2$ or $R'_2$, $R_3$ or $R'_3$ and $R_4$ or $R'_4$, $R_5$ or $R'_5$ and $R_6$ or $R'_6$, and $R_7$ or $R'_7$ and $R_8$ or $R'_8$ are independently selected wherein one "R" group of the pair is an alkyl, alkenyl, alkynyl, cycloalkyl or cycloalkenyl radical and the other "R" group on the adjacent carbon atom of the macrocycle is a substituted alkyl, substituted alkenyl, substituted alkynyl, substituted cycloalkyl or substituted cycloalkenyl radical wherein the substituents are independently selected from the group consisting of —$OR_{10}$, —$NR_{10}R_{11}$, —$COR_{10}$, —$CO_2R_{10}$, —$CONR_{10}R_{11}$, —O—(—($CH_2$)$_a$—O)$_b$—$R_{10}$, —$SR_{10}$, —$SOR_{10}$, —$SO_2R_{10}$, —$SO_2NR_{10}R_{11}$, —$N(OR_{10})(R_{11})$, —$P(O)(OR_{10})(OR_{11})$, —$P(O)(OR_{10})(R_{11})$ and —$OP(O)(OR_{10})(OR_{11})$;

wherein $R_{10}$ and $R_{11}$ are independently selected from the group consisting of hydrogen and alkyl groups, and a and b are integers independently selected from 1 to 6; and wherein the remaining "R" groups are hydrogen or, optionally, are independently selected from the group consisting of alkyl, alkenyl, alkynyl, cycloalkyl, cycloalkenyl, cycloalkylalkyl, cycloalkylcycloalkyl, cycloalkenylalkyl, alkylcycloalkyl, alkenylcycloalkyl, alkylcycloalkenyl, alkenylcycloalkenyl, heterocyclic, aryl and aralkyl radicals and radicals attached to the α-carbon of α-amino acids; or $R_1$ or $R'_1$ and $R_2$ or $R'_2$, $R_3$ or $R'_3$ and $R_4$ or $R'_4$, $R_5$ or $R'_5$ and $R_6$ or $R'_6$, $R_7$ or $R'_7$ and $R_8$ or $R'_8$ and $R_9$ or $R'_9$ and R or R' together with the carbon atoms to which they are attached independently form a saturated, partially saturated or unsaturated cyclic having 3 to 20 carbon atoms; or R or R' and $R_1$ or $R'_1$, $R_2$ or $R'_2$ and $R_3$ or $R'_3$, $R_4$ or $R'_4$ and $R_5$ or $R'_5$, $R_6$ or $R'_6$ and $R_7$ or $R'_7$, and $R_8$ or $R'_8$ and $R_9$ or $R'_9$ together with the carbon atoms to which they are attached independently form a nitrogen containing heterocycle having 2 to 20 carbon atoms provided that when the nitrogen containing heterocycle is an aromatic heterocycle which does not contain a hydrogen attached to the nitrogen, the hydrogen attached to the nitrogen in said formula, which nitrogen is also in the macrocycle and the R groups attached to the same carbon atoms of the macrocycle are absent;

wherein M is Mn; and wherein X, Y and Z are ligands independently selected from the group consisting of halide, oxo, aqua, hydroxo, alcohol, phenol, dioxygen, peroxo, hydroperoxo, alkylperoxo, arylperoxo, ammonia, alkylamino, arylamino, heterocycloalkyl amino, heterocycloaryl amino, amine oxides, nitric oxide, cyanide, cyanate, thiocyanate, isocyanate, isothiocyanate, alkyl nitrile, aryl nitrile, alkyl isonitrile, aryl isonitrile, nitrate, nitrite, azido, alkyl sulfonic acid, aryl sulfonic acid, alkyl sulfoxide, aryl sulfoxide, alkyl aryl sulfoxide, alkyl sulfenic acid, aryl sulfenic acid, alkyl sulfinic acid, aryl sulfinic acid, alkyl thiol carboxylic acid, aryl thiol carboxylic acid, alkyl thiol thiocarboxylic acid, aryl thiol thiocarboxylic acid, alkyl carboxylic acid, aryl carboxylic acid, urea, alkyl urea, aryl urea, alkyl aryl urea, thiourea, alkyl thiourea, aryl thiourea, alkyl aryl thiourea, sulfate, sulfite, bisulfate, bisulfite, thiosulfate, thiosulfite, hydrosulfite, alkyl phosphonic acid, aryl phosphonic acid, alkyl phosphinic acid, aryl phosphinic acid, alkyl phosphinous acid, aryl phosphinous acid, phosphate, thiophosphate, phosphite, pyrophosphite, triphosphate, hydrogen phosphate, dihydrogen phosphate, alkyl guanidino, aryl guanidino, alkyl aryl guanidino, alkyl carbamate, aryl carbamate, alkyl aryl carbamate, alkyl thiocarbamate, aryl thiocarbamate, alkylaryl thiocarbamate, alkyl dithiocarbamate, aryl dithiocarbamate, alkylaryl dithiocarbamate, bicarbonate, carbonate, perchlorate, chlorate, chlorite, hypochlorite, perbromate, bromate, bromite, hypobromite, tetrahalomanganate, tetrafluoroborate, hexafluoroantimonate, hypophosphite, iodate, periodate, metaborate, tetraaryl borate, tetra alkyl borate, tartrate, salicylate, succinate, citrate, ascorbate, saccharinate, amino acid, hydroxamic acid, thiotosylate, and anions of ion exchange resins, or the corresponding anions thereof, or X, Y and Z are independently attached to one or more of the "R" groups and n is 0 or 1.

2. The compound of claim 1, wherein at least one pair of "R" groups on adjacent carbon atoms of the macrocycle selected from the group consisting of $R_9$ or $R'_9$ and R or R', $R_1$ or $R'_1$ and $R_2$ or $R'_2$, $R_3$ or $R'_3$ and $R_4$ or $R'_4$, $R_5$ or $R'_5$ and $R_6$ or $R'_6$, and $R_7$ or $R'_7$ and $R_8$ or $R'_8$ are substituted alkyl, substituted alkenyl, substituted alkynyl, substituted cycloalkyl or substituted cycloalkenyl radicals wherein the substituents are independently selected from the group consisting of $-OR_{10}$, $-NR_{10}R_{11}$, $-COR_{10}$, $-CO_2R_{10}$, $-CONR_{10}R_{11}$, $-O-(-(CH_2)_a-O)_b-R_{10}$, $-SR_{10}$, $-SOR_{10}$, $-SO_2R_{10}$, $-SO_2NR_{10}R_{11}$, $-N(OR_{10})(R_{11})$, $-P(O)(OR_{10})(OR_{11})$, $-P(O)(OR_{10})(R_{11})$ and $-OP(O)(OR_{10})(OR_{11})$; and wherein the remaining "R" groups are hydrogen or, optionally, are independently selected from the group consisting of alkyl, alkenyl, alkynyl, cycloalkyl, cycloalkenyl, cycloalkylalkyl, cycloalkylcycloalkyl, cycloalkenylalkyl, alkylcycloalkyl, alkenylcycloalkyl, alkylcycloalkenyl, alkenylcycloalkenyl, heterocyclic, aryl and aralkyl radicals and radicals attached to the α-carbon of α-amino acids; or $R_1$ or $R'_1$ and $R_2$ or $R'_2$, $R_3$ or $R'_3$ and $R_4$ or $R'_4$, $R_5$ or $R'_5$ and $R_6$ or $R'_6$, $R_7$ or $R'_7$ and $R_8$ or $R'_8$, and $R_9$ or $R'_9$ and R or R' together with the carbon atoms to which they are attached independently form a saturated, partially saturated or unsaturated cyclic having 3 to 20 carbon atoms; or R or R' and $R_1$ or $R'_1$, $R_2$ or $R'_2$ and $R_3$ or $R'_3$, $R_4$ or $R'_4$ and $R_5$ or $R'_5$, $R_6$ or $R'_6$ and $R_7$ or $R'_7$ and $R_8$ or $R'_8$, and $R_9$ or $R'_9$ together with the carbon atoms to which they are attached with the carbon atoms to which they are attached independently form a nitrogen containing heterocycle having 2 to 20 carbon atoms provided that when the nitrogen containing heterocycle is an aromatic heterocycle which does not contain a hydrogen attached to the nitrogen, the hydrogen attached to the nitrogen in said formula, which nitrogen is also in the macrocycle and the R groups attached to the same carbon atoms of the macrocycle are absent.

3. The compound of claim 2, wherein $R_{10}$ and $R_{11}$ are hydrogen.

4. The compound of claim 2, wherein said substituents are independently selected from the group consisting of $-OR_{10}$ and $-NR_{10}R_{11}$.

5. The compound of claim 4, wherein the "R" groups of the at least one pair of "R" groups on adjacent carbon atoms of the macrocycle are substituted alkyl groups.

6. The compound of claim 2, wherein the "R" groups of the at least one pair of "R" groups on adjacent carbon atoms of the macrocycle are substituted alkyl groups.

7. The compound of claim 6, wherein said substituents on the at least one pair of "R" groups on adjacent carbon atoms of the macrocycle are independently $-OR_{10}$.

8. The compound of claim 7, wherein the complex is:

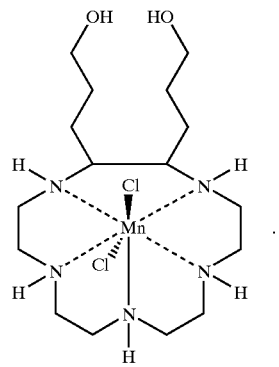

9. The compound of claim 1, wherein at least one pair of "R" groups on adjacent carbon atoms of the macrocycle selected from the group consisting of $R_9$ or $R'_9$ and R or R', $R_1$ or $R'_1$ and $R_2$ or $R'_2$, $R_3$ or $R'_3$ and $R_4$ or $R'_4$, $R_5$ or $R'_5$ and $R_6$ or $R'_6$, and $R_7$ or $R'_7$ and $R_8$ or $R'_8$, are independently selected wherein one "R" group of the pair is an alkyl, alkenyl, alkynyl, cycloalkyl or cycloalkenyl radical and the other "R" group on the adjacent carbon atom of the macrocycle is a substituted alkyl, substituted alkenyl, substituted alkynyl, substituted cycloalkyl or substituted cycloalkenyl radical wherein the substituents are independently selected from the group consisting of $-OR_{10}$, $-NR_{10}R_{11}$, $-COR_{10}$, $-CO_2R_{10}$, $-CONR_{10}R_{11}$, $-O-(-(CH_2)_a-O)_b-R_{10}$, $-SR_{10}$, $-SOR_{10}$, $-SO_2R_{10}$, $-SO_2NR_{10}R_{11}$, $-N(OR_{10})(R_{11})$, $-P(O)(OR_{10})(OR_{11})$, $-P(O)(OR_{10})(R_{11})$ and $-OP(O)(OR_{10})(OR_{11})$; and wherein the remaining "R" groups are hydrogen or, optionally, are independently selected from the group consisting of alkyl, alkenyl, alkynyl, cycloalkyl, cycloalkenyl, cycloalkylalkyl, cycloalkylcycloalkyl, cycloalkenylalkyl, alkylcycloalkyl, alkenylcycloalkyl, alkylcycloalkenyl, alkenylcycloalkenyl, heterocyclic, aryl and aralkyl radicals and radicals attached to the α-carbon of α-amino acids; or $R_1$ or $R'_1$ and $R_2$ or $R'_2$, $R_3$ or $R'_3$ and $R_4$ or $R'_4$, $R_5$ or $R'_5$ and $R_6$ or $R'_6$, $R_7$ or $R'_7$ and $R_8$ or $R'_8$, and $R_9$ or $R'_9$ and R or R' together with the carbon atoms to which they are attached independently form a saturated, partially saturated or unsaturated cyclic having 3 to 20 carbon atoms; or R or R' and $R_1$ or $R'_1$, $R_2$ or $R'_2$ and $R_3$ or $R'_3$, $R_4$ or $R'_4$ and $R_5$ or $R'_5$, $R_6$ or $R'_6$ and $R_7$ or $R'_7$, and $R_8$ or $R'_8$, and $R_9$ or $R'_9$ together with the carbon atoms to which they are attached independently form a nitrogen containing heterocycle having 2 to 20 carbon atoms provided that when the nitrogen containing heterocycle is an aromatic heterocycle which does not contain a hydrogen attached to the nitrogen, the hydrogen attached to the nitrogen in said formula, which nitrogen is also in the macrocycle and the R groups attached to the same carbon atoms of the macrocycle are absent.

10. The compound of claim 9, wherein $R_{10}$ and $R_{11}$ are hydrogen.

11. The compound of claim 9, wherein said substituents are independently selected from the group consisting of $-OR_{10}$ and $-NR_{10}R_{11}$.

12. The compound of claim 11, wherein one "R" group of the at least one pair of "R" groups on adjacent carbon atoms of the macrocycle is an alkyl group and the other "R" group on the adjacent carbon atom of the macrocycle is a substituted alkyl group.

13. The compound of claim 9, wherein one "R" group of the at least one pair of "R" groups on adjacent carbon atoms of the macrocycle is an alkyl group and the other "R" group on the adjacent carbon atom of the macrocycle is a substituted alkyl group.

14. The compound of claim 13, wherein said substituent on the carbon atom of the at least one pair of "R" groups on adjacent carbon atoms of the macrocycle which is a substituted group is —$OR_{10}$.

15. The compound of claim 1, wherein X, Y and Z are independently selected from the group consisting of halide, alkyl sulfonic acid, aryl sulfonic acid, alkyl sulfenic acid, aryl sulfenic acid, alkyl sulfinic acid, aryl sulfinic acid, alkyl thiol carboxylic acid, aryl thiol carboxylic acid, alkyl thiol thiocarboxylic acid, aryl thiol thiocarboxylic acid, alkyl carboxylic acid, aryl carboxylic acid, alkyl phosphonic acid, aryl phosphonic acid, alkyl phosphinic acid, aryl phosphinic acid, alkyl phosphinous acid, aryl phosphinous acid, amino acid, hydroxamic acid, nitrate and bicarbonate anions.

16. A pharmaceutical composition in unit dosage form useful for dismutating superoxide comprising:
  (a) a therapeutically or prophylactically effective amount of a complex of claim 1; and
  (b) a nontoxic, pharmaceutically acceptable carrier, adjuvant or vehicle.

17. A method of treating a disease or disorder which is mediated, at least in part, by superoxide comprising administering to a subject in need of such treatment, a therapeutically, prophylactically, or resuscitative effective amount of a complex of claim 1.

18. The method of claim 17, wherein said disease or disorder is selected from the group consisting of ischemic reperfusion injury, surgically-induced ischemia, inflammatory bowel disease, rheumatoid arthritis, atherosclerosis, thrombosis, platelet aggregation, oxidant-induced tissue injuries and damage, osteoarthritis, psoriasis, organ transplant rejections, radiation-induced injury, stroke, acute pancreatitis, insulin-dependent diabetes mellitus, adult and infantile respiratory distress, metastasis and carcinogenesis.

19. The method of claim 18, wherein said disease or disorder is selected from the group consisting of ischemic reperfusion injury, stroke, atherosclerosis and inflammatory bowel disease.

20. The method of claim 19, wherein said complex is represented by the formula:

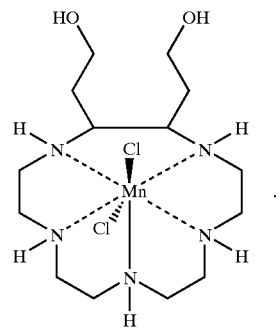

21. A method of using a complex of claim 1, comprising formulating said complex into a pharmaceutical composition and administering said composition to a subject in need of treatment of a disease or disorder which is mediated at least in part by superoxide or oxygen radicals derived therefrom.

* * * * *

UNITED STATES PATENT AND TRADEMARK OFFICE
CERTIFICATE OF CORRECTION

PATENT NO. : 6,525,041 B1
DATED : February 25, 2003
INVENTOR(S) : William L. Neumann et al.

It is certified that error appears in the above-identified patent and that said Letters Patent is hereby corrected as shown below:

Column 1,
Lines 41 and 46, add -- . -- after "al" and before ","
Line 43, add -- , -- after "Weiss"
Line 65, add -- , -- after "Factor" and before """

Column 2,
Line 5, italicize "in vivo"
Line 32, replace "-O-(-($CH_2$)$_a$-O)$_b$-$R_{10}$" with -- -O-(-($CH_2$)$_a$-O$_b$-$R_{10}$ --

Column 3,
Line 1, replace "-O-(-($CH_2$)$_a$" with -- -O-(-($CH_2$)$_a$-O)$_b$ --.
Line 2, replace "O)$_b$-$R_{10}$" with -- O)$_b$-$R_{10}$ --.
Line 8, add a space between "R'$_7$" and "and"
Line 54, add a comma after "for example"

Column 4,
Line 5, add a space between "," and "alkyl"
Line 28, add a space between "," and "Y"
Line 43, replace "-O-(-($CH_2$)$_a$-O)$_b$-$R_{10}$" with -- -O-(-($CH_2$)$_a$-O$_b$-$R_{10}$ --

Column 5,
Line 24, replace "-O-(-($CH_2$)$_a$-O)$_b$-$R_{10}$" with -- -O-(-($CH_2$)$_a$-O$_b$-$R_{10}$ --

Column 7,
Replace lines 26-38 with (new chemical needed due replacing R'$_6$ and $R_6$ with R'$_8$ and $R_8$)
Line 52, replace "P" with -- p --
Line 46, should $HO_2$ be $HO_2$ (both occurrences)
Line 47, should $O_2$ be $O_2$ (first occurrence)
Line 49, should $O_2/O_2$ be $O_2/O_2$ and $HO_2$ be $HO_2$

UNITED STATES PATENT AND TRADEMARK OFFICE
CERTIFICATE OF CORRECTION

PATENT NO.   : 6,525,041 B1
DATED        : February 25, 2003
INVENTOR(S)  : William L. Neumann et al.

It is certified that error appears in the above-identified patent and that said Letters Patent is hereby corrected as shown below:

Columns 15-18,
Replace Scheme B with the following:

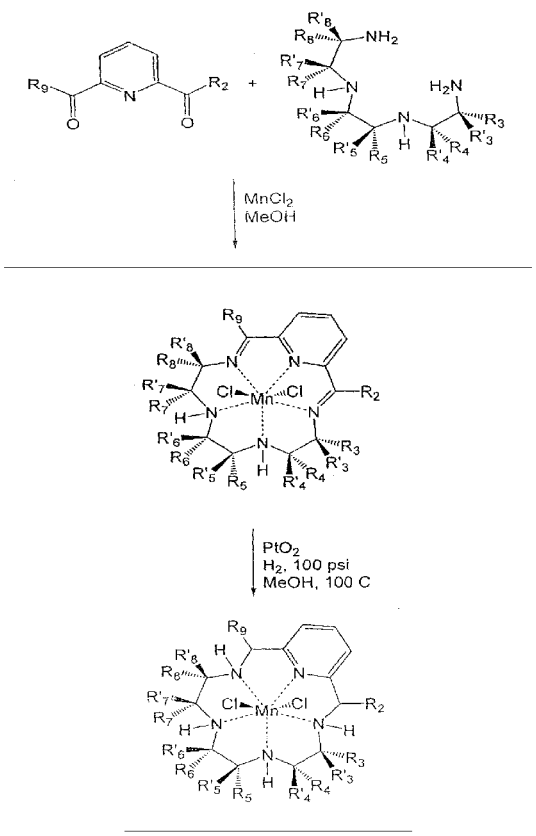

Column 29,
Lines 44, 46, 48 and 63, italicize "in vacuo"

Column 30,
Lines 19, 38, 41 and 44, italicize "in vacuo"
Line 31, replace "Application" with -- Number --
Line 55, replace "entaazacyclopentadecane-3,8-dione" with -- pentaazacyclopentadecane-3,8-dione --

UNITED STATES PATENT AND TRADEMARK OFFICE
CERTIFICATE OF CORRECTION

PATENT NO. : 6,525,041 B1
DATED : February 25, 2003
INVENTOR(S) : William L. Neumann et al.

It is certified that error appears in the above-identified patent and that said Letters Patent is hereby corrected as shown below:

Column 31,
Lines 7, 32 and 51, italicize "in vacuo"
Line 28, add -- . -- after "minutes"
Line 36, italicize "in"
Line 37, italicize "vacuo"

Column 33,
Line 24 and 35, replace "$k_{obs}$" with -- $k_{obs}$ --
Lines 28 and 33, replace "$k_{cal}$" with -- $k_{cal}$ --
Line 39, replace "$(Z_n)$" with -- $(Z_n)$ --
Line 59, replace "-O-(-$(CH_2)_a$-" with -- -O-(-$(CH_2)_a$- --
Line 60, replace "O)$_b$-$R_{10}$" with -- O)$_b$-$R_{10}$ --

Column 34,
Line 9, replace "-O-(-$(CH_2)_a$-O)$_b$-$R_{10}$" with -- -O-(-$(CH_2)_a$-O$_b$-$R_{10}$ --

Column 35,
Line 24, replace "-O-(-$(CH_2)_a$-O)$_b$-$R_{10}$" with -- -O-(-$(CH_2)_a$-O)$_b$-$R_{10}$ --

Column 36,
Line 29, replace "-O-(-$(CH_2)_a$-" with -- -O-(-$(CH_2)_a$- --
Line 30, replace "O)$_b$-$R_{10}$" with -- O)$_b$-$R_{10}$ --

Column 38,
Line 10, replace "19" with -- 17 --

Signed and Sealed this

Seventeenth Day of August, 2004

JON W. DUDAS
*Acting Director of the United States Patent and Trademark Office*